(12) United States Patent
Richt et al.

(10) Patent No.: US 9,372,903 B1
(45) Date of Patent: Jun. 21, 2016

(54) DATA LINEAGE IN AN INTELLIGENT DATA INTEGRATION SYSTEM

(71) Applicant: Monsanto Technology LLC, St. Louis, MO (US)

(72) Inventors: Ryan Jerry Richt, St. Louis, MO (US); Christopher Allen Taylor, Ballwin, MO (US)

(73) Assignee: Monsanto Technology LLC, St. Louis, MO (US)

( * ) Notice: Subject to any disclaimer, the term of this patent is extended or adjusted under 35 U.S.C. 154(b) by 385 days.

(21) Appl. No.: 13/910,302

(22) Filed: Jun. 5, 2013

Related U.S. Application Data

(60) Provisional application No. 61/655,715, filed on Jun. 5, 2012.

(51) Int. Cl.
*G06F 17/30* (2006.01)
(52) U.S. Cl.
CPC .................................. *G06F 17/30563* (2013.01)
(58) Field of Classification Search
CPC ....................... G06F 17/30563; G06F 17/30607
USPC ........... 707/602, 736, 756, 803, 804; 717/116
See application file for complete search history.

(56) References Cited

U.S. PATENT DOCUMENTS

| | | | |
|---|---|---|---|
| 7,747,981 B2 | 6/2010 | Gray | |
| 2002/0035569 A1* | 3/2002 | Clark | G06F 8/70 707/999.102 |
| 2004/0183800 A1 | 9/2004 | Peterson | |
| 2005/0189414 A1 | 9/2005 | Fano et al. | |
| 2009/0157700 A1* | 6/2009 | Van Vugt | H04L 41/0213 707/999.1 |
| 2010/0070448 A1 | 3/2010 | Omoigui | |
| 2011/0004864 A1 | 1/2011 | Gray | |
| 2011/0264642 A1 | 10/2011 | Mital et al. | |

OTHER PUBLICATIONS

Marcio Katsumi Oikawa, et al., GenFlow: Generic flow for integration, management and analysis of molecular biology data, Genetics and Molecular Biology, Brazilian Society of Genetics, www.sbg.orgbr, published 2004, pp. 691-964, vol. 27, issue 4, Brazil.

Jessica Severin, et al., eHive: An Artificial Intelligence workflow system for genomic analysis, BMC Bioinformatics, published 2010, 11:240, 15 pages, www.biomedcentral.com/1471-2105/11/240.

Daniel Shegoegue, et al., Object-oriented biological system integration: a SARS coronavirus example, Bioinformatics, published Feb. 24, 2005, pp. 2502-2509, vol. 21 No. 10, Oxford, England.

* cited by examiner

*Primary Examiner* — Hares Jami
(74) *Attorney, Agent, or Firm* — Senniger Powers LLP; James E. Davis

(57) ABSTRACT

A computer-executed method includes storing in a data store data attributes, data objects, and a data analysis tool (DAT). Each data object has an attribute set and an identifier set. The method includes identifying each data object that has an attribute set comprising a data attribute matching each reference data attribute associated with the DAT, and selecting an identified data object as an input data object for the DAT. The DAT generates a new data object as a function of the input data object, which includes analyzing the input data object with reference to an auxiliary data object and creating an identifier set for the new data object that includes an identifier of the new data object for distinguishing the new data object from each other data object in the data store, and the identifier of the auxiliary data object. The new data object is stored in the data store.

17 Claims, 10 Drawing Sheets

DATA LINEAGE IN AN INTELLIGENT DATA INTEGRATION SYSTEM

BACKGROUND

Many companies and research institutions already possess an unmanageably rich, deep and extensive menagerie of valuable raw data. However, these companies and research institutions are often ill-equipped to deal with the data in a comprehensive and meaningful way. It is becoming more expensive to integrate, process, and analyze such a large amount of data compared to the expense of generating the data itself. This problem is particularly evident in the biotechnology industry, and is also evident in other industries, including finance, pharmaceuticals, insurance, operations research, advertising, military intelligence/security, social media analytics and medicine.

For example, in the field of biotechnology, a company (or researcher) may have generated data relating to quantitative RNA sequencing, gene expression and gene regulation, protein crystal structures, protein interaction data, high throughput phenotyping (leaf surface area, root morphology, shoot mass, etc), gene expression data from eukaryotic or bacterial cell systems, leading to the creation of high resolution genetic maps, genotypic marker data and trait association data, and whole reference genome sequencing with a myriad of annotations. The data sets may be across stresses (nitrogen deficit, water deficit, high salt, etc), species (corn, soy, sugarcane, etc), populations (historical, geographic, etc), tissues (root, shoot, meristem, etc), and time (developmental or seasonal/historical). With next-generation sequencing, high throughput automated processing (via imaging or robotics) in growth chambers or the like, biotechnology and/or pharmaceutical companies and researchers will generate more and more insightful data than ever before. Such data may assist in the generation of as new vegetable varieties, protein-optimized antibiotics, individualized medical diagnostics and therapeutics, as well as complete insect, viral, plant or bacterial genomes. When RNA-seq based coding and non-coding gene annotations and expression profiles are included along with whole genome nucleosome positioning, DNA methylation, histone modification and other epigenetic data and single and combinatorial gene knockouts the deluge of data and the current inability to comprehensively analyze it and make it useful are made abundantly clear.

DNA sequencing is the highest possible resolution measurement in the life sciences and, until recently, was the most costly. Since the completion of the human genome project in 2001, the cost of DNA sequencing has dropped more than 10,000 fold. This has been achieved by a radical increase in data output that continues to double every 6 months—much faster than Moore's 18 month law for microprocessor speed doubling. As a result, biotechnology and medical applications are quickly becoming DNA sequencing-based assays. A genetic sequence is the ultimate biomarker—it is the indivisible "quanta" of the life sciences. These technological changes affect everything from the discovery and screening efforts of academics, agro-biotechnology firms, and pharmaceutical giants to diagnostic and screening efforts of the USDA, diagnostics labs, and hospitals. Most recognizable university and life science companies have a genomics program rooted in sequencing. In a few years, the costs will be sufficiently low to spawn entirely new direct-to-consumer markets and help realize true "personalized medicine."

DNA sequencing, which outputs raw data, has in some ways brought more problems than solutions. Although next generation sequencing provides higher throughput, it is now in smaller, less informative pieces (~100 letter long DNA strings called "reads") that are more difficult to analyze. A single HiSeq DNA sequencer (available from Illumina LLC) can produce an overwhelming one terabyte of data per week. Even with a history of genomics expertise and an army of bioinformaticians, it could take a company more than a month to perform the most cursory analysis on a single such HiSeq run. Traditional organizational and software paradigms for dealing with this large amount of data simply do not scale to the level of complexity and richness modern integrated analyses necessitate. Moreover, it is necessary to integrate the data, which means comparing new data to all historical data, and that is precisely where the problem lies: comparing everything with everything else gets into the realm of N2 problems that take enormous computing resources to begin to analyze.

SUMMARY

Embodiments of the present invention relate to a system that provides intelligent data integration. In particular, the system enables a plurality of individual, independent, and unaffiliated data analysis tools (DATs) to self-assemble into a workflow. The workflow is comprised of a plurality of independent processes. Each process comprises identifying from a potentially large data store, such as a database, a particular data object as an input data object for a particular DAT, and executing the DAT to generate a separate data object as an output data object. The processes, and thereby the DATs, link themselves together when the output data object generated in one process is used as an input data object for another process. In this way, an arbitrarily complicated web of processes may be integrated to perform a workflow, and the analysis performed by the DAT of each process is aggregated so that an aggregate work product emerges.

In one embodiment, the IDIS stores a plurality of data attributes, a plurality of data objects, and at least one DAT in a data store. Each data object has an attribute set comprising one or more of the plurality of data attributes. Each data object is also associated with an identifier set. The identifier set of a particular data object comprises at least an identifier (ID) of that particular data object that distinguishes the particular data object from each other data object of the plurality of data objects. The DAT is associated with at least one reference data attribute of the plurality of data attributes, and at least one auxiliary data object of the stored plurality of data objects.

In operation, each data object of the plurality of stored data objects that has an attribute set comprising a data attribute that matches each of the reference data attributes associated with the DAT is identified. In turn, one or more of the identified data objects are selected as input data object(s) for the DAT. The DAT generates a new data object as a function of the input data object(s) for the DAT. In generating the new data object, the DAT analyzes the input data object(s) with reference to the auxiliary data object associated with the DAT, and creates an identifier set for the new data object. The identifier set includes an identifier of the new data object that distinguishes it from each other data object of the plurality of stored data objects. The identifier set also includes the ID of the auxiliary data object referenced by the DAT in generating the new data object. In one embodiment, the identifier set also includes the ID or, alternatively, the identifier set of the input data object(s) analyzed by the DAT. As such, the identifier set of the new data object provides data for tracking the data objects that were accessed in the generation of the new data object. This tracking data enables data objects to be easily recreated, and the work product created from a data object to be efficiently identified.

Other objects and features will be apparent and pointed out hereinafter.

BRIEF DESCRIPTION OF THE DRAWINGS

The following drawings form part of the present specification and are included to further demonstrate certain aspects of the present invention. Embodiments of the invention may be better understood by reference to one or more of these drawings in combination with the detailed description of specific embodiments presented herein.

Corresponding reference characters indicate corresponding parts throughout the drawings.

DETAILED DESCRIPTION

Figure 1:
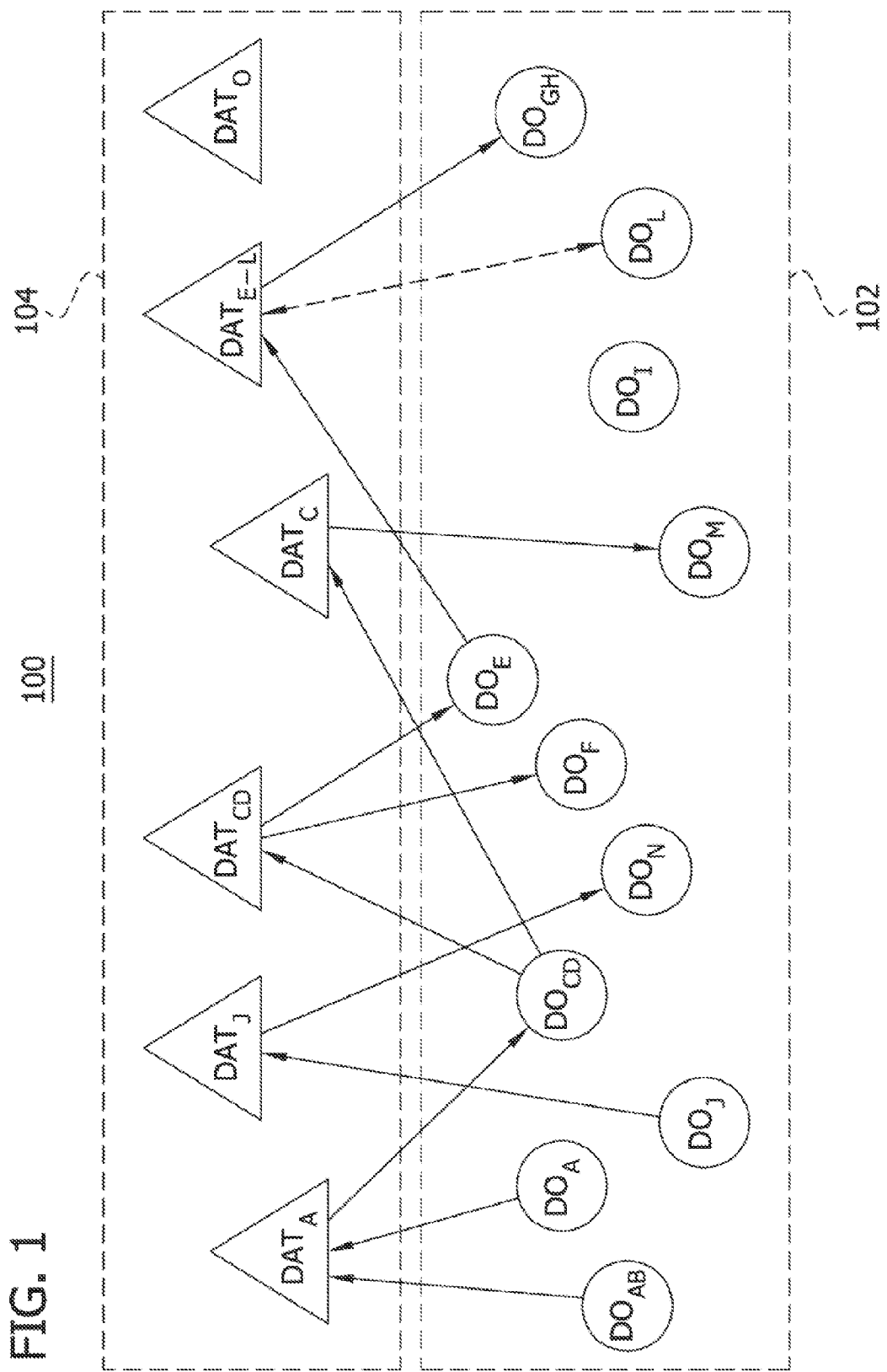
FIGS. 1 and 2 are block diagrams of an exemplary system model in accordance with an embodiment of the invention.

The present disclosure relates to an intelligent data integration system (IDIS). FIG. 1 is a diagram that illustrates, by example, a system model 100 for the IDIS. As illustrated, the system model comprises data objects (DOs) and data analysis tools (DATs). Each data object and data analysis tool is a self-contained, distinct entity. In particular, each data object is a non-executable data item. Each data analysis tool is a set of executable instructions for interacting with (e.g., analyzing, generating, referencing, querying) data objects to perform a task. As explained below, the components and features of the system model enable IDIS to integrate the tasks performed by the DATs to provide an aggregate data product.

The illustrated system model 100 includes data objects $DO_{AB}$, $DO_A$, $DO_J$, $DO_{CD}$, $DO_N$, $DO_F$, $DO_E$, $DO_M$, $DO_I$, $DO_L$, and $DO_{GH}$, and data analysis tools $DAT_A$, $DAT_J$, $DAT_{CD}$, $DAT_C$, and $DAT_{E \to L}$. Each data analysis tool defines data object criteria, analyzes one or more data objects existing in the IDIS that satisfy the defined data object criteria, and generates one or more new data objects as a function of the analyzed data objects. Accordingly, the one or more data objects existing in the IDIS that satisfy the defined data object criteria and are analyzed by a particular DAT represent input data object(s) with respect to the particular DAT, and the one or more new data objects that are generated by the particular DAT represent output data object(s) with respect to the particular DAT. A DAT may also reference a DO in the analysis of the input DO or the generation of the output DO. A DO that is referenced (e.g., queried) by a particular DAT represents an auxiliary DO with respect to the particular DAT.

Each connection line shown in FIG. 1 that connects a DAT with a DO represents an interaction between those connected components. Specifically, the DOs that are connected to a particular DAT via a solid line with an arrow pointing toward the particular DAT are input DOs (collectively, "input set") for the particular DAT. Similarly, the DOs that are connected to a particular DAT via a solid line with an arrow pointing away from the particular DAT are output DOs (collectively, "output set") for the particular DAT. A DO connected to a particular DAT via a dashed connection line is an auxiliary DO for the particular DAT.

In accordance with the illustrated system model 100, $DAT_A$ operates to analyze $DO_{AB}$, and $DO_A$ and to generate $DO_{CD}$ as a function of $DO_{AB}$ and $DO_A$. As such, $DO_{AB}$, and $DO_A$ function as input DOs for $DAT_A$, and $DO_{CD}$ is an output DO of $DAT_A$. $DAT_J$ operates to analyze $DO_J$ and to generate $DO_N$ as a function of $DO_J$. As such, $DO_J$ functions as an input DO for $DAT_J$, and $DO_N$ is an output DO of $DAT_J$. $DAT_{CD}$ operates to analyze $DO_{CD}$ and to generate $DO_F$ and $DO_E$ as a function of $DO_{CD}$. As such, $DO_{CD}$ functions as an input DO for $DAT_{CD}$, and $DO_F$ and $DO_E$ are output DOs of $DAT_{CD}$. $DAT_C$ operates to analyze $DO_{CD}$ and to generate $DO_M$ as a function of $DO_{CD}$. As such, $DO_M$ functions as an input DO for $DAT_C$, and $DO_M$ is an output DO of $DAT_C$. $DAT_{E \to L}$ operates to analyze $DO_E$ and to generate $DO_{GH}$ as a function of $DO_E$. In analyzing $DO_E$ and/or generating $DO_{GH}$, $DAT_{E \to L}$ references $DO_L$ for information. As such, $DO_J$ functions as an input DO for $DAT_J$, $DO_L$ functions as an auxiliary DO for $DAT_{E \to L}$, and $DO_{GH}$ is an output DO of $DAT_{E \to L}$.

The IDIS may include a DO, such as DO, shown in the illustrated system model 100, that does not satisfy the criteria of any of the existing DATs in the IDIS (i.e., DO is unmatched). Similarly, the IDIS may include a DAT, such as $DAT_A$ shown in the illustrated system model 100, which is inoperative because it has data object criteria that is not satisfied by any of the existing DOs in the IDIS. However, the set of data objects and data analysis tools existing in the IDIS is dynamic in that data objects and data analysis tools can be added to and removed from the IDIS. As described above, a DO can be added to the IDIS as a result of being generated by a DAT. A DO can also be added to the IDIS by uploading the DO from another computing system, or by manually (i.e., via user input) entering the DO into the IDIS. Once a DO is added to the IDIS, if the DO satisfies the data object criteria defined by any of the DATs existing in the IDIS, those DATs may analyze the newly added DO. Thus, a DAT that is inoperative becomes operative if a DO is added to the IDIS that satisfies the data object criteria defined by that DAT. A DAT can be manually (i.e., via user input) added to the IDIS. Once a DAT is added to the IDIS, the newly added DAT can analyze DOs that satisfy the data object criteria defined by the newly added DAT. Thus, an existing DO that is unmatched becomes matched if a DAT is added to the IDIS that has data object criteria that is satisfied by the existing DO. As such, as new DOs and DATs are added to the IDIS, new interactions between DOs and DATs are enabled so that additional analyses are performed by the DATs.

Figure 2:
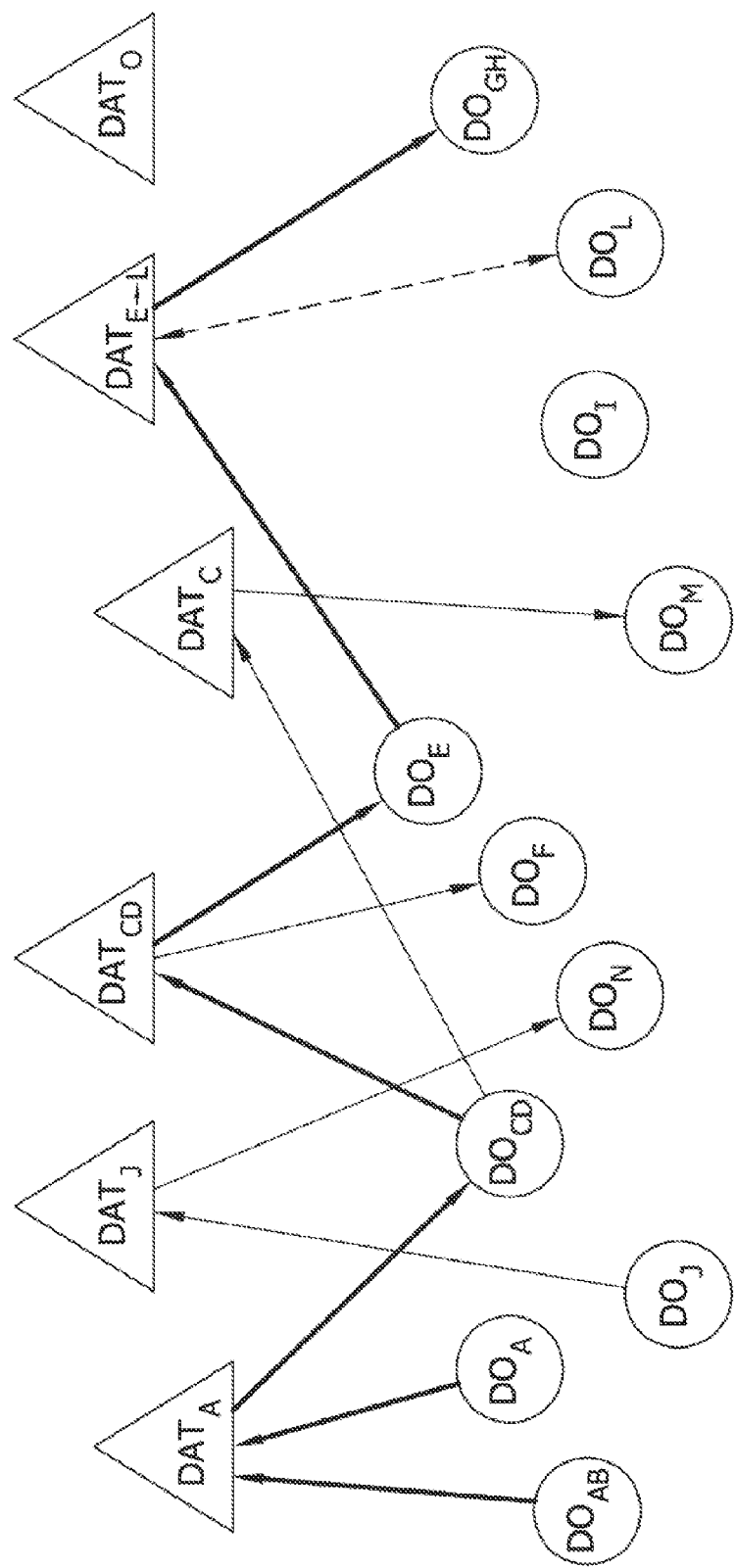

Referring generally to FIG. 2, the IDIS system model enables the analyses provided by a plurality of the DATs to be aggregated without ever requiring an affiliation between each of the DATs (e.g., local affiliation) or of the plurality of DATs (e.g., global affiliation). In particular, each DAT is a stand-alone program that is executed as an independent entity. As indicated by the lack of connection lines between the DATs in the system model 100, the DATs are autonomous and do not interact with each other. Moreover, each DAT can be defined exclusively with respect to each of the other DATs. In other words, each DAT may be created without knowledge of or reference to each of the other DATs. The analyses performed by two unaffiliated DATs are aggregated when an output DO generated by one DAT functions as the input DO of another DAT.

FIG. 2 highlights an exemplary aggregation of analyses performed by the unaffiliated DATs of the system model 100. As illustrated, the analyses performed by unaffiliated $DAT_A$, $DAT_{CD}$, and $DAT_{E \rightarrow L}$ are aggregated as a function of common input and output data objects. In particular, $DAT_A$ defines data object criteria, which is met by $DO_{AB}$ and $DO_A$, and $DAT_A$ thereby analyzes $DO_{AB}$ and $DO_A$. $DAT_A$ generates $DO_{CD}$, which reflects a result of the analysis of $DO_{AB}$ and $DO_A$, and $DO_{CD}$ is added to IDIS. $DO_{CD}$ meets the data object criteria defined by $DAT_{CD}$, so after $DO_{CD}$ is added to IDIS it is analyzed by $DAT_{CD}$. And, $DAT_{CD}$ generates $DO_F$ and $DO_E$ which reflect a result of the analysis of $DO_{CD}$, and $DO_F$ and $DO_E$ are added to IDIS. Although $DO_F$ is unmatched when it is added to IDIS, $DO_E$ is matched with $DAT_{E \rightarrow L}$ because it meets the criteria defined by $DAT_{E \rightarrow L}$. Accordingly, $DAT_{E \rightarrow L}$ analyzes $DO_E$, and in doing so references $DO_L$, and then generates $DO_{GH}$ which reflects a result of the analysis. Thus, although $DAT_A$, $DAT_{CD}$, and $DAT_{E \rightarrow L}$ are completely unaffiliated with each other, in accordance with the system model 100, they self-assemble to produce an aggregate work product ($DO_{GH}$) from initial data objects ($DO_{AB}$ and $DO_A$). For example, the aggregate work product may represent a useful assessment, which is produced through the assembly of DATs from initial raw data.

Figure 3:
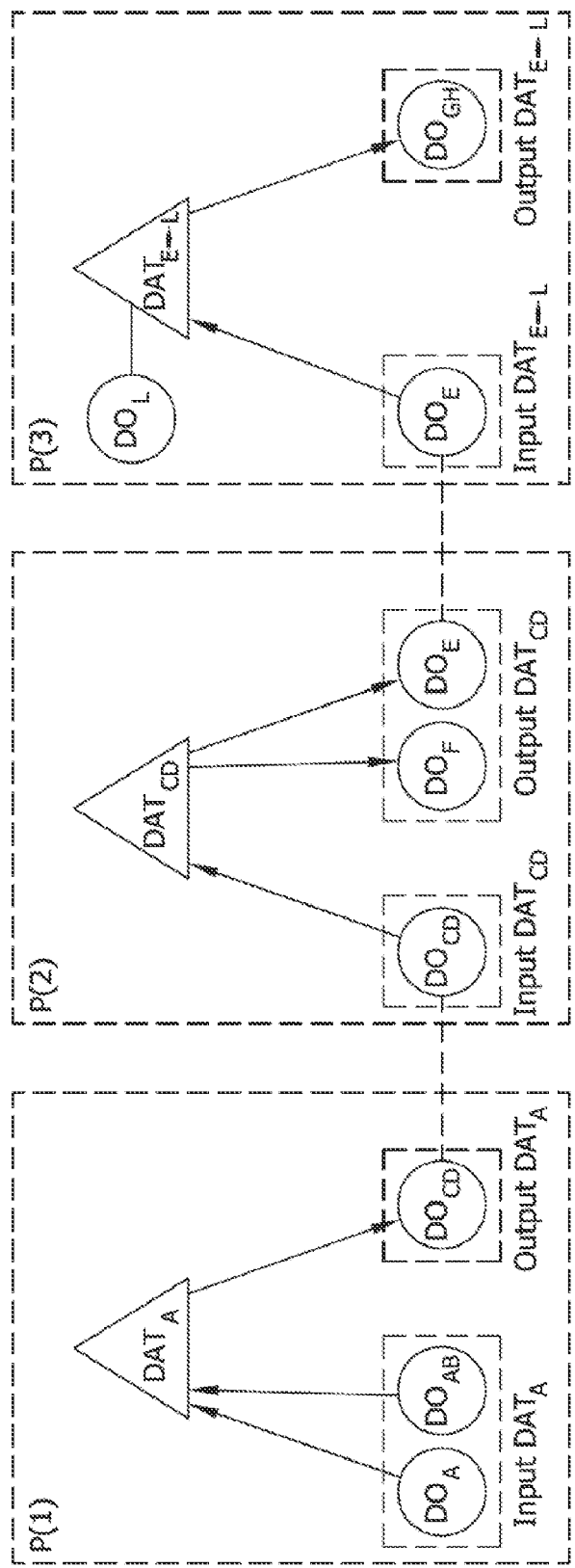
FIG. 3 is a process diagram for the exemplary system model illustrated in FIGS. 1 and 2.

Referring generally to FIG. 3, through the execution of DATs, IDIS operates to create and perform workflows, wherein IDIS simultaneously creates and performs each of the workflows. A workflow is formed of a plurality of independent and unaffiliated processes P(x). Each process includes identifying a DO that satisfies the data object criteria defined by a particular DAT as an input DO for that DAT, and executing the particular DAT so that it analyzes the input DO and generates an output DO reflecting a result of the analysis. The processes effectively concatenate when the output DO generated in one process is an input DO utilized by another process. Thus, a series of processes P(x), where x=1, 2 . . . n, and n is the total number of processes in the series, self assemble when a first process P(1) identifies the input DO for the DAT of that process, and each subsequent process P(x), for x>1, identifies as an input DO, the DO that was generated as an output DO from process P(x−1).

FIG. 3 illustrates a workflow that is simultaneously created and performed by the IDIS in an embodiment that includes the exemplary DOs and DATs described in connection with FIG. 2. In particular, once $DO_{AB}$ and $DO_A$ are received by IDIS, IDIS implements a first process P(1). In the first process, IDIS identifies as input DOs for $DAT_A$, and executes $DAT_A$. The execution of $DAT_A$ results in the generation of $DO_{CD}$, which is an output DO of $DAT_A$. Once $DO_{CD}$ is generated IDIS implements a second process P(2). In the second process, IDIS identifies $DO_{CD}$ as an input DO for $DAT_{CD}$, and executes $DAT_{CD}$. The execution of $DAT_{CD}$ results in the generation of $DO_F$ and $DO_E$, which are output DOs of $DAT_{CD}$. Once $DO_E$ is generated IDIS implements a third process P(3). In the third process, IDIS identifies $DO_E$ as an input DO for $DAT_{E \rightarrow L}$, and executes $DAT_{E \rightarrow L}$. The execution of $DAT_{E \rightarrow L}$ results in the generation of $DO_{GH}$, which is an output DO of $DAT_{E \rightarrow L}$. Thus, the required processes and order thereof for generating $DO_{GH}$ from $DO_{AB}$ and $DO_A$ are simultaneously determined and implemented by IDIS.

Figure 4:
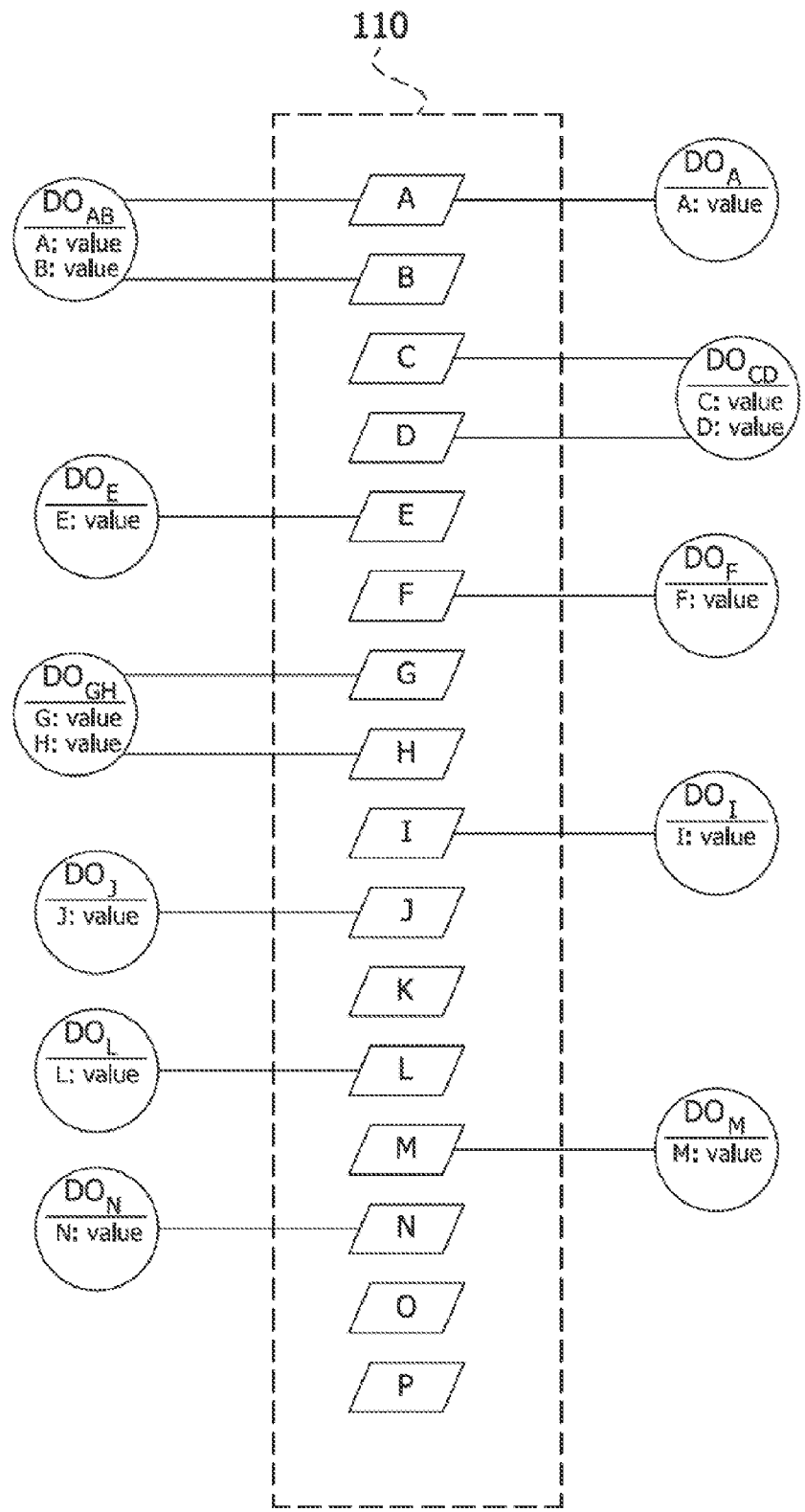
FIG. 4 is a block diagram of an aspect of an exemplary system model in accordance with an embodiment of the invention.

Referring generally to FIG. 4, in one embodiment, in addition to DOs and DATs, the system model 100 includes a plurality of data attributes that are used to define the data objects. Specifically, each data attribute is a particular parameter which can have various values. For example, a data attribute of color could have values such as red, blue, yellow, etc. In accordance with the system model, a data object can be defined exclusively by a set of one or more data attributes and specific values for each of the one or more data attributes. In other words, the system model enables each data object to consist only of the set of one or more data attributes and the specific values for each of the data attributes of the set. As such, there is no formal "type" associated with a data object. As described in further detail below, this aspect of the system model may be implemented using "duck typing" or "structural typing." In traditional programming systems, value "slots" have an associated "type" which defined the range of possible values that fit into that slot. Common types include Integer, Floating-point or decimal number, String, Arrays or Matrices, etc. In traditional object-oriented languages, every class also defines a new type. For instance in Scala we could define a "Duck" class with several properties:

class Duck(val countOfFeathers: Int, val colorOfBill: String, val quackDuration: Float)

A variable such as:

val plucky: Duck= . . .

is constrained to only be allowed to contain instances of the class Duck, that instance having the type "Duck." An example of assigning a new duck:

val plucky: Duck=new Duck(542, "yellow-orange", 2.4)

By contrast, object-oriented duck typing in dynamic languages or structural typing in strong-typed languages considers values to be members of a given type *not* because they have an associated named type such as "Duck" but only on the basis of that object value conforming to a notion of a Duck. This conformity can be on the basis of having certain methods or having certain properties, etc. In Scala, one could define a structural type for our duck like this:

type DuckLike={val countOfFeathers: Int, val colorOfBill: String, val quackDuration: Float}

And this type would consider our "Swan" class to conform to "Duck" on the basis of having these properties, even though it is not strictly an instance of a "Duck" class or a subclass of Duck:

class Swan(val isBlack: Boolean, val countOfFeathers: Int, val colorOfBill: String, val quackDuration: Float)

This is now valid, demonstrating structural typing:

val plucky: DuckLike=new Swan(true, 685, "orange", 1.2)

FIG. 4 illustrates an exemplary plurality of data attributes 110, which are included in an embodiment of the system model 100. The exemplary plurality of data attributes 110 includes data attributes A, B, C, D, E, F, G, H, J, K, L, M, N, O, P, and I. The exemplary data objects illustrated in the system model 100 each have a data attribute set comprising one or more of the exemplary plurality of data attributes 110 and a value for each of those data attributes. The subscript of each illustrated data object is indicative of the data attributes included in the data attribute set of that data object. For example, $DO_A$ has a data attribute set consisting of data attribute A, and $DO_{AB}$ has a data attribute set consisting of data attributes A and B. In accordance with this example, one data attribute (i.e., data attribute A) may be used to define a plurality of different data objects (i.e., data objects may have common data attributes), and the value of the data attribute for the different data objects may be the same or different.

In one embodiment, the IDIS employs a plurality of data attributes, such as the exemplary plurality of data attributes 110, as a library of data attributes. The library may include data attributes (e.g., data attributes K, O, and P) that are not included in the set of data attributes of any of the data objects existing in the IDIS at a given point in time. Data objects are created (e.g., added to the IDIS) by selecting one or more of the data attributes from the library of data attributes and defining (i.e., assigning) values for the selected data attributes. Thus, a data attribute must be defined in the library of data attributes before it can be used to create a data object. In this way, the plurality of data attributes (e.g., library of data attributes) supply an ontology for the IDIS, with each data attribute being an ontology term. This ontology provides structure and a quasi-standardization (e.g., controlled vocabulary) for the creation and analysis of the data objects. In one embodiment, the library of data attributes is dynamic in that data attributes (i.e., ontology terms) can be added to and removed from the library. Thus, the ontology of the IDIS may continuously evolve.

Additional standardization may be achieved by defining each of the plurality of data attributes in the library to specify a computer programming data type for the values that can be used for that data attribute to form a data object. Accordingly, a data attribute may be defined to require that each and every value corresponding to that data attribute is an integer, a floating point, a fixed point, a string, an array, a record, a union, an object, a set, a queue, Boolean, a tree, etc. For example, data attribute A, illustrated in FIG. 4, may be defined in the library so that any value assigned to data attribute A is required to be a string. Thus, the value of A in $D_{OA}$ and the value of A in $D_{AB}$ is a specific string.

In an exemplary embodiment, the IDIS defines a superclass of data attributes, referenced as "OntologyTerm." The OntologyTerm superclass establishes parameters that must be defined by each data attribute in the library (i.e., each ontology term). In one example, the OntologyTerm superclass requires each data attribute in the library to define a description parameter ("desc") that describes the data attribute (i.e., a name for the data attribute) and a type ("type T") that specifies a computer programming data type for the values that can be assigned to that data object. In accordance therewith, each data attribute in the library is established as a class (e.g., subclass) of the OntologyTerm superclass and provides a particular name and a particular type. For example, data attribute A and data attribute B are defined, in pseudo-Scala, as follows:

class A
    extends OntologyTerm("desc"){type T=String}
    class B
    extends OntologyTerm("desc")(type T=Int)

One or more superclasses of data objects may be defined to simplify coding required to create data objects and incorporate additional structure into the IDIS. For example, one superclass, "DataObject1" may be defined for creating data objects having a data attribute set consisting of one data attribute, and another superclass, "DataObject2" may be defined for creating data objects having a data attribute set consisting of two data attributes. In accordance therewith, one or more classes of data objects are defined for each superclass. Each class of data objects specifies a name and the data attributes in the data attribute set. As noted above, instances of the data objects (referred herein as "data objects") are created by selecting a data object class (e.g., specifying the name of the data object class) and defining values for the data attributes in that data attribute set. The creation and implementation of data object classes provides additional structure to the IDIS.

In one example, a class of data objects having a set of data attributes consisting of data attribute A is defined, in pseudo-Scala, as follows:

class $DO_A$(args: Option[(String)])
    extends DataObject1[A](args){
    def this( )=this (None)
    }

An exemplary class of data objects having a set of data attributes consisting of data attributes A and B is defined, in pseudo-Scala, as follows:

class $DO_{AB}$(args: Option[(String, Int)])
    extends DataObject2[A, B](args){
    def this( )=this (None)
    }

Instances of the $DO_A$ and $DO_{AB}$ classes are created and added to the database, in pseudo-Scala, as follows:

val instance$DO_A$=new $DO_A$(Some(blue)) repository.add (instance$DO_A$)
    val instance$DO_{AB}$=new $DO_{AB}$(Some(blue, 31)) repository.add (instance$DO_{AB}$)

As previously discussed in connection with FIGS. 1-3, the IDIS includes data analysis tools (DATs) which each define data object criteria and, when executed, analyze data objects matching the data object criteria. In one embodiment, the data object criteria indicates at least one data attribute ("reference data attribute"), and the IDIS identifies data objects (e.g., instances of data objects) having a data attribute that matches the reference data attribute for analysis by the DAT. In one embodiment, the data object criteria establishes a specific data attribute (e.g., ontology term, data attribute class, library data attribute) as the reference data attribute. For example, $DAT_A$ may define data attribute A (e.g., class A) as the reference data attribute. $DO_A$ and $DO_{AB}$ (i.e., instance$DO_A$ and instance$DO_{AB}$) match the reference data attribute since the data attribute sets of both data objects include data attribute A.

Additionally or alternatively, the data object criteria for a DAT may indicate the reference data attribute by specifying a data object. The data attribute(s) of the specified data object are the reference data attribute(s) associated with that DAT. For example, $DAT_A$ may establish $DO_A$ (e.g., class $DO_A$) as the data object criteria. The data attribute set for $DO_A$ consists of data attribute A, so data attribute A is the reference data attribute associated with $DAT_A$. $DO_A$ and $DO_{AB}$ (i.e., instance $DO_A$ and instance$DO_{AB}$) match the reference data attribute since the data attribute sets of both data objects include data attribute A.

Additionally or alternatively, the data criteria for a DAT may indicate a Boolean combination (e.g., AND, OR, NOT, XOR, NAND) of reference data attributes. In this case, the IDIS identifies data objects that have a data attribute set that satisfies the Boolean combination of reference data attributes for analysis by the DAT. For example, $DAT_{CD}$ may have data object criteria that specifies data attribute C AND data attribute D as the Boolean combination of reference data attributes. $DO_{CD}$ matches the Boolean combination of reference data attributes since the data attribute set for $DO_{CD}$ includes both data attribute C and data attribute D. Alternatively, $DAT_{CD}$ may have data object criteria that specifies data attribute C OR data attribute D as the Boolean combination of reference data attributes. $DO_{CD}$ matches the Boolean combination of reference data attributes since the data attribute set for $DO_{CD}$ includes at least one of data attribute C and data attribute D.

The IDIS identifies a data attribute of a data object as matching a reference data attribute if the data attribute of the data object is identical (e.g., data attribute of the data object is member of the reference data attribute class). In one embodiment, the IDIS also identifies the data attribute of the data object as matching the reference data attribute if the data attribute of the data object and the reference data attribute have a semantic lexical relationship. For example, the data attribute of the data object and the reference data attribute are considered to match if the data attribute and reference data attribute have a cognitive synonym relationship, a hyponym/hypernym relationship, or meronym/holonym relationship.

Additionally or alternatively, the IDIS may employ a mapping scheme that relates (e.g., maps) data attributes of the IDIS together. For example, the mapping scheme may be based on a semantic lexical relationship between the data attributes in accordance with the above discussion, other similarity/commonality between the data attributes, and/or a user-defined relationship. In accordance therewith, the IDIS identifies the data attribute of the data object as matching the reference data attribute if the data attribute of the data object is mapped to the reference data attribute.

DATs may be added to the system via user input. The user input provides the instructions for defining the data object criteria, analyzing an input data object, and generating a new data object. Thus, the user input provides instructions establishing reference data object(s) and/or reference data attributes, computations to perform with respect to an input data object, and data attribute(s) and value(s) for assigning to those data attribute(s) that define one or more output data objects. When a DAT is submitted via user input to the IDIS, it must be compiled in accordance with principles generally known in the art, before it is executable by the IDIS. In one embodiment, the IDIS validates the submitted DAT at compile time by enforcing the ontology described above. In particular, the IDIS verifies that the reference data object(s) and/or reference data attributes are data object(s) and/or data attributes, respectively, that exist in the IDIS. Likewise, the IDIS verifies that the data attribute(s) for the output data object(s) exist in the IDIS, and that the value(s) for assigning to the data attribute(s) satisfy any criteria that is specified by those data attribute(s) existing in the IDIS (e.g., assigned value is the programming data type specified by the data attribute).

In accordance with the exemplary data attributes and data objects illustrated in FIG. 4, in one example, the IDIS includes library data attributes A, B, C, and D and have computer programming data types assigned thereto as integer, string, a floating point, and a string, respectively. The IDIS includes, among others, data object classes: class $DO_A$ which requires instances to have a data attribute set that explicitly includes only data attribute A; class $DO_{AB}$ which requires instances to have a data attribute set that explicitly includes only data attributes A and B; and class $DO_{CD}$ which requires instances to have a data attribute set that explicitly includes only data attributes C and D. The data attribute sets can include additional hidden data attributes (i.e., non-explicit data attributes).

An exemplary submitted DAT is defined as follows
Class $DAT_A$ extends DataAnalysisTool [$DO_A$]{//reference DO . . . def run (DataObject: $DO_A$) { . . . . }}//analysis steps
Repository.add(new $DO_{CD}$(Some (C, D))) //output DO
}
Since class $DO_A$ is the reference data object, at compile time, the IDIS verifies that class $DO_A$ exists in the IDIS. In addition, any data attributes that are specified by the DAT to be analyzed are verified as being data attributes for class $DO_A$. Thus, in this case, the only data attribute that can be specified by the DAT for input data object analysis is data attribute A. The IDIS also verifies that class $DO_{CD}$ exists since the submitted DAT is coded to generate instances $DO_{CD}$, and that data attributes C and D are data attributes for class $DO_{CD}$ data objects.

By enforcing the ontology of the IDIS, the validation measures provide system efficiency and prevent improper operations, errors, and crashes in the IDIS. Once the DAT is validated by the IDIS, the DAT is added to the IDIS and may be executed. As such, the IDIS identifies matching data object instances ($DO_A$ and $DO_{AB}$) for the new DAT, and when executed, the new DAT generates data object instance(s) $DO_{CD}$.

In one embodiment, the IDIS comprises a memory and a processor. The memory includes non-transitory computer readable media for operating as a data store such that it can store components of the IDIS including the data attributes, the data objects, and the data analysis tools. Thus, the components (e.g., data attributes, DOs, DATs) described above as existing in the IDIS are those that are stored in a data store of the IDIS. The memory includes non-transitory computer readable media that store computer executable instructions, in addition to those of the data analysis tools, for operating the IDIS as described in the present disclosure. The memory may include volatile and/or non-volatile memory, and may comprise internal storage media and/or external storage media. Internal exemplary storage media include RAM, ROM, EEPROM, flash memory and/or other internal storage media known in the art. Exemplary external storage media include memory sticks, CD-ROM, digital versatile disks (DVD), magnetic cassettes, magnetic tape, magnetic disks and/or other storage media known in the art.

The processor is configured to communicate with memory via a wired or wireless connection and to execute the instructions stored in the memory. It should be noted that the processor and the memory may comprise a plurality of processors and a plurality of memories. For example, in one embodiment, the processor and the memory are a computer cluster, which comprises a plurality of loosely connected computing devices (e.g., processors and memories) that operate together such that they are viewed as a single system.

In general, the IDIS includes computer executable instructions for creating data objects via user/device input and through the execution of DATs, and for executing the DATs. As further detailed below, in one embodiment, the IDIS also includes computer executable instructions for periodically or continuously identifying matching data objects for the DATs, scheduling execution of the DATs to analyze each of the identified matching data objects, and querying data objects based on user initiated search criteria.

Figure 5:
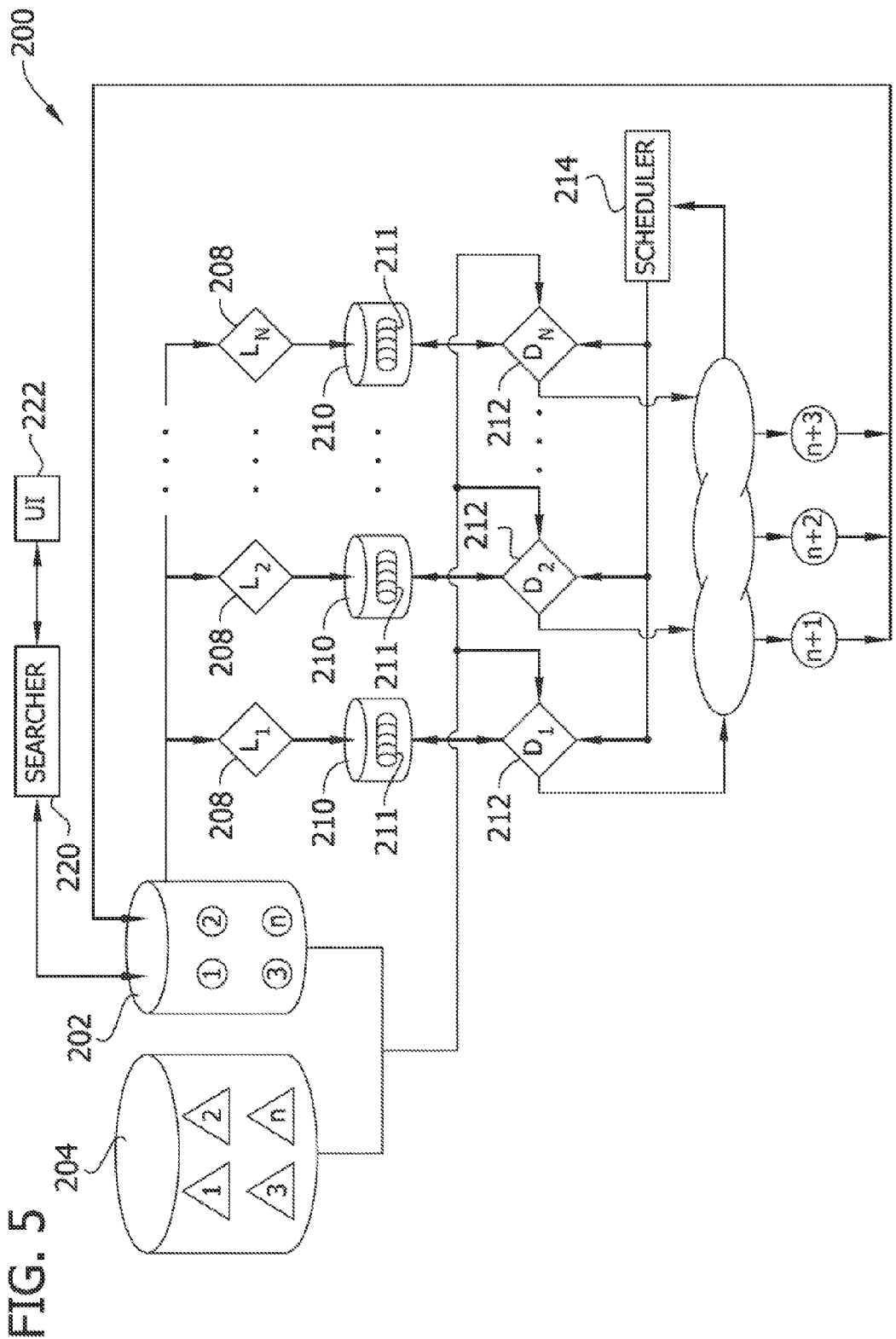
FIG. 5 is a block diagram of an exemplary system in accordance with an embodiment of the invention.

Referring to FIG. 5, one embodiment of an implementation of the IDIS is generally indicated at 200. As explained above, the IDIS comprises data objects (DOs) and data analysis tools (DATs), each of which is a self-contained, distinct entity. In the illustrated embodiment, the DOs are stored in a DO data store 202 (e.g., one or more databases) and the DATs are stored in a DAT database 204 (broadly, a data store). It is understood that the DOs and DATs may be stored in the same data store, that the DOs and DATs may be stored in other types of data stores, beside databases 202, 204. In one non-limiting example, the databases 202, 204 are part of a data management system, such as schema-less data management system as disclosed below.

As set forth above, each DO includes a set of one or more data attributes, and each DAT defines data object criteria (e.g., one or more reference data attributes), analyzes one or more DOs existing in the IDIS that satisfy the defined data object criteria, and generates one or more new DOs as a function of each analyzed data object. Based on this system model 100, the illustrated implementation of the IDIS generally includes a listening and enqueing component 208 assigned to each DAT in the database 204 for identifying DO(s) in the database 202 that satisfy the criteria of the corresponding DAT, a collection 210 of DO(s) for each DAT that includes the DO(s) identified by the corresponding listener, a dispatcher 212 assigned to each DAT for selecting a DO in the collection to be analyzed by the corresponding DAT, and a task scheduler 214 for scheduling the DAT tasks on available nodes of a computer cluster. It should be noted that although the components are illustrated as separate entities, the components are limited to such a configuration. The present invention contemplates that the functions performed by a plurality of the components may be performed by a single component, and/or the functions performed by a single component may be performed by multiple components.

In the illustrated embodiment, each DAT has one listening and enqueing component 208 assigned to it, although it is understood that more than one listening and enqueuing component may be assigned to a single DAT, and/or one listening and enqueuing component may be assigned to a plurality of DATs. Each listening and enqueing component 208 operates to automatically identify DOs in the database 202 that satisfy the criteria set by the corresponding DAT. In particular, the DOs each include a set of data attributes, and the DATs each have one or more reference data attributes (i.e., criteria) associated therewith. Accordingly, each listening and enqueing component 208 automatically identifies (e.g., filters, queries, etc.) DOs in the database 202 that have data attributes matching the one or more reference data attributes associated with the corresponding DAT. Each listening and enqueing component 208 may be automatically generated (i.e., created and executed) when the corresponding DAT is uploaded to the IDIS. That is, the IDIS may include a listener-generating software application, whereupon when a DAT is uploaded to the IDIS, the listener-generating software application is automatically executed to generate a listener that identifies DOs for the newly added DAT based on the criteria set by the DAT.

In the illustrated embodiment, when a DO ("identified DO") in the database 202 is identified by the listening and enqueing component 208 as satisfying the data object criteria set by the corresponding DAT, the listening and enqueuing component saves a task object in the corresponding collection 210 associated with the DAT. Each collection 210 may be its own database or may be logically separate from the other collections. The task object includes the ID of the identified data object (i.e., a pointer to the data object) and the ID of the particular DAT (i.e., a pointer to the DAT). The listening and enqueing component 208 also assigns an approximate sequence number to the task object, and the task object is enqueued in the collection 210, with respect to other task objects in the corresponding collection, based on its approximate sequence number. In one embodiment, the listening and enqueing component 208 reads the queue 211 of task objects in the collection 210 and assigns an approximate sequence number to a new task object based on the last (i.e., the largest) approximate sequence number in the queue that is read by the listening and enqueuing component. In one example of this embodiment, the collection 210 is a database, reads of which may be in parallel, to allow for non-blocking enqueuing into the queue, but writes to which are serialized. Accordingly, the queue reads by the listening and enqueing component 208 may be stale, and as such, the task objects in the queue 211 may have the same approximate sequence number.

In another embodiment, the listening and enqueing component 208 assigns approximate sequence numbers to the task objects based on an order in which the identified data objects were identified by the listening and enqueing component 208. In yet another embodiment, the listening and enqueing component 208 assigns approximate sequence numbers to the task objects based on an order in which the identified data objects were stored in the IDIS. In another embodiment, the listener assigns approximate sequence numbers to the task objects based on size required for the storing each of the identified data objects in the database. In yet another embodiment, the listening and enqueing component 208 assigns approximate sequence numbers to the task objects based on total number of prior accesses by a DAT for each of the identified data objects. In another embodiment, the listening and enqueing component 208 assigns approximate sequence numbers to the task objects based on, for each identified data object of the collection 210, a cumulative total number of generated result sets from a search (as explained below) in which the identified data object is included. In yet another example, where user-feedback is determined from the generated result sets, the listening and enqueing component 208 assigns approximate sequence numbers to the task objects based on received user feedback. Other ways of ordering the identified DOs to be analyzed by the corresponding DAT associated with the collection 210 do not depart from the scope of the present invention.

In one embodiment, each collection 210 may have a maximum size (i.e., a maximum memory allocation). In one example, the maximum size of each collection 210 may be dynamic, whereby the maximum size of the collection changes, depending on pre-selected parameters. For example, the maximum size of the collection 210 may be adjusted as a function of a rate that the task objects are added to the collection, and/or the maximum size of the collection may be adjusted as a function of the rate that the task objects of the collection are selected for analysis by the corresponding DAT. Other parameters may be used for adjusting the maximum size of the collection 210. It is also understood that the maximum size of each collection 210 may be static.

As set forth above, the task scheduler 214 schedules the DAT tasks to be run on available nodes of a computer cluster (illustrated as a cloud). The task scheduler 214 is in communication with the computer cluster and is notified when a node becomes available. Once notified, the task scheduler 214 selects a DAT, using a predetermined scheduling methodology, for execution on the available node. Any suitable scheduling method for allocating and/or ordering processing time to the respective DATs, relative to the other DATs, may be implemented. Suitable scheduling methodologies include first in first out (FIFO) and shortest job first (SJF). In accordance with the predetermined scheduling methodology, the task scheduler 214 communicates with the dispatcher 212 that is assigned to the collection 210 that contains the DOs that were identified in accordance with the selected DAT. The task scheduler 214 communicates to the selected dispatcher 212 that the DAT associated with the dispatcher has been selected to run on an available node.

Each dispatcher 212, when notified to do so by the task scheduler 214, selects one task object (which relates to the previously identified DOs) from the queue 211 in the collection 210 to be analyzed by the corresponding DAT. In one embodiment, the dispatcher 212 selects a task object based on the approximate sequence numbers assigned to the task objects. For example, the dispatcher 212 may select the task object that is next in line in the queue 211 based on the approximate sequence numbers assigned to the task objects. The selected task object from the queue 211 of task objects is removed (e.g., logically removed) from the queue. In one example, the dispatcher 212 requests a predefined number of task objects from the queue 211 based on the approximate sequence numbers assigned to the task objects. For example, during an initial request, the dispatcher 212 may request ten

(10) task objects that are next in line the queue 211. This is done to facilitate the selection process, since the reads by the dispatcher 212 may be stale, as explained above.

Upon selecting a task object from the corresponding collection 210, the dispatcher communicates with the DO database and the DAT database so that the selected DAT is run on the available node of the computer cluster with the DO (i.e., "selected DO") referenced by the selected task object as an input DO. As set forth above, the result of the analysis of the selected DO by the DAT is the generation of at least one additional DO. This newly generated DO is saved to the DO database and is available for identification by existing and future listeners for analysis by the DATs. In addition to its own unique ID, the newly generated DO includes the IDs of each input DO used by the DAT that created the newly generated DO. As explained below, this data lineage is used when searching (i.e., querying) the DO database 202.

A working example of the IDIS implementation in FIG. 5 will now be disclosed. In this example, all DOs and DATs are stored in a schema-less (or NoSQL) data management system called Apache CouchDB (hereinafter, "CouchDB"). It is understood that the IDIS may utilize other data management systems and databases without departing from the scope of the present invention. The DOs and the DATs are stored in one or more databases in CouchDB as JSON (JavaScript Object Notation) documents. (CouchDB is referred to as a document-oriented database because the data is stored as individual documents.) Accordingly, the DOs and DATs include data attributes and values associated with the data attributes. Moreover, each DO and DAT has an ID attribute, and a unique value associated with the ID attribute (i.e., a randomly generated sequence). For example, source code, in JavaScript, for an exemplary DO may read as follows:

```
{
"_id": "04ae4502jhf4hgh . . . ",
"number": "15",
"color": "Blue"
}
```

Using the above exemplary source code, the ID attribute is indicated by the term "_id," the value associated with the ID attribute is "04ae4502jhf4hgh . . . . "; the two data attributes are "number" and "color," and the values associated with the data attributes are "15" and "Blue" respectively.

In one example, an application programming interface (API) (e.g., Ektorp) is used to interface with CouchDB. For example, the DOs can be added to the CouchDB database by writing code (e.g., Java or Scala), as set forth above, so that the API can map the code (e.g., object relational mapping) as a JSON document in the database. The same can be done for DATs, wherein DATs are added to the CouchDB database by writing code (e.g., Java or Scala), as set forth above, so that the API can map the code (e.g., object relational mapping) as a JSON document in the database. A repository layer can also be built over the API, as is generally known in the art.

When adding a DAT to the IDIS, a listening and enqueuing component may be automatically initiated. In this example, the listening and enqueuing component includes a filter function, which subscribes to the data attributes that are indicated by the reference data attributes of the DAT. The filter function of the listener identifies DOs having data attributes that match the reference data attributes associated with the particular DAT (as disclosed above herein), and then saves instances of the identified DOs to a staging database. It is understood that in one embodiment the staging database may be omitted. The following is code, written in JavaScript, for an exemplary filter function:

```
function(doc){
  return(
    doc.attributeA !==undefined &&
    doc.attributeB !==undefined &&)
  )
}
```

The listening and enqueuing component also includes a task queuing function. The task queuing function of the listener automatically generates the task objects based on the DOs in the staging database within CouchDB. In particular, the listening and enqueuing component generates task objects that include the ID (i.e., the value associated with the "_id" attribute) of the identified DO and the ID (i.e., the value associated with the "_id" attribute) of the associated DAT. The listening and enqueuing component reads the queue of task objects in the collection database and assigns an approximate sequence number to each new task object based on the last (i.e., the largest) approximate sequence number in the queue that is read by the listening and enqueuing component. The queue reads by the listening and enqueuing component may be stale, and as such, the task objects in the queue may have the same approximate sequence number.

A task scheduler schedules the tasks to be run on available nodes of a computer cluster, and dispatchers, each of which is assigned to a collection database, retrieve the task objects from the collection database. The task scheduler is in communication with the computer cluster and is notified when a node becomes available. Once notified, the task scheduler selects a DAT, using a predetermined scheduling methodology, for execution on the available node. Suitable scheduling method for allocating and/or ordering processing time to the respective DATs, relative to the other DATs are set forth above. In accordance with the predetermined scheduling methodology, the task scheduler communicates with the dispatcher that is assigned to the collection database that contains the DOs that were identified in accordance with the selected DAT. The task scheduler communicates to the selected dispatcher that the DAT associated with the dispatcher has been selected to run on the available node.

Each dispatcher, when notified to do so by the task scheduler, selects one task object (which relates to the previously identified DO) from the queue in the collection database to be analyzed by the corresponding DAT. The dispatcher selects the task object that is next in line in the queue based on the approximate sequence numbers assigned to the task objects. The selected task object from the queue of task objects is removed (e.g., logically removed) from the queue. In one example, the dispatcher requests a predefined number of task objects from the collection based on the approximate sequence numbers assigned to the task objects. For example, during an initial request, the dispatcher may request ten (10) task objects that are next in line the queue. This is done to facilitate the selection process, since the reads by the dispatcher may be stale because the tasks have already been claimed. Upon selecting a task object from the corresponding queue, the selected DAT is run on the available node of the computer cluster with the selected DO (as referenced by the task object) as an input. The result of the analysis of the selected DO by the DAT is the generation of at least one additional DO. This newly generated DO is saved to the DO database and is available for identification by existing and future listeners for analysis by the DATs.

In one example, the illustrated implementation 200 includes the DOs and DATs shown in FIG. 2 and executes the interactions indicated by the connection lines shown therein. In accordance therewith, each of the data objects ($DO_{AB}$, $DO_A$, $DO_J$, $DO_{CD}$, $DO_N$, $DO_F$, $DO_E$, $DO_M$, $DO_P$, $DO_L$, and $DO_{GH}$) is associated with an identifier set of one or more identifiers. The identifier set may be stored in the data object, or the identifier set may be stored in the data store, separately from the data object. In one embodiment, the identifier set for a data object includes an ID (respectively, ID-$DO_{AB}$, ID-$DO_A$, ID-$DO_J$, ID-$DO_{CD}$, ID-$DO_N$, ID-$DO_F$, ID-$DO_E$, ID-$DO_M$, ID-$DO_I$, ID-$DO_L$, and ID-$DO_{GH}$) for uniquely identifying that data object (e.g., distinguishing itself) from each other data object existing in the IDIS. In one embodiment, if the data object is not generated by a DAT (e.g., added to the IDIS manually or via computing device), the IDIS is configured to create an identifier set having the ID of the data object, and associate the identifier set with the data object. For these data objects, the identifier set may consist only of the ID of the data object, or may include additional data provided manually, via the computing device, and/or by the IDIS itself. If the data object is generated by a DAT (referred to as "generating DAT"), the generating DAT may create (i.e., establish) an identifier set for the data object. For these data objects, in addition to its own unique ID, the identifier set of each particular data object may include IDs of one or more data objects accessed by DAT(s) in order to create the particular data object. For example, for each particular data object, the auxiliary data object(s) accessed (i.e., referenced) by the generating DAT may be tracked. Thus, in one embodiment, in addition to its own unique ID, the identifier set of each particular data object includes the ID(s) of any auxiliary data object(s) that were referenced by the DAT that generated the particular data object. Accordingly, for the DOs and DATs shown in FIG. 2, the identifier set for $DO_{GH}$ includes its own identifier ID-$DO_{GH}$, and the identifier of $DO_L$ (ID-$DO_L$) since $DO_L$ is an auxiliary data object accessed by $DAT_{E \to L}$ which generated $DO_{GH}$.

Figure 6A:
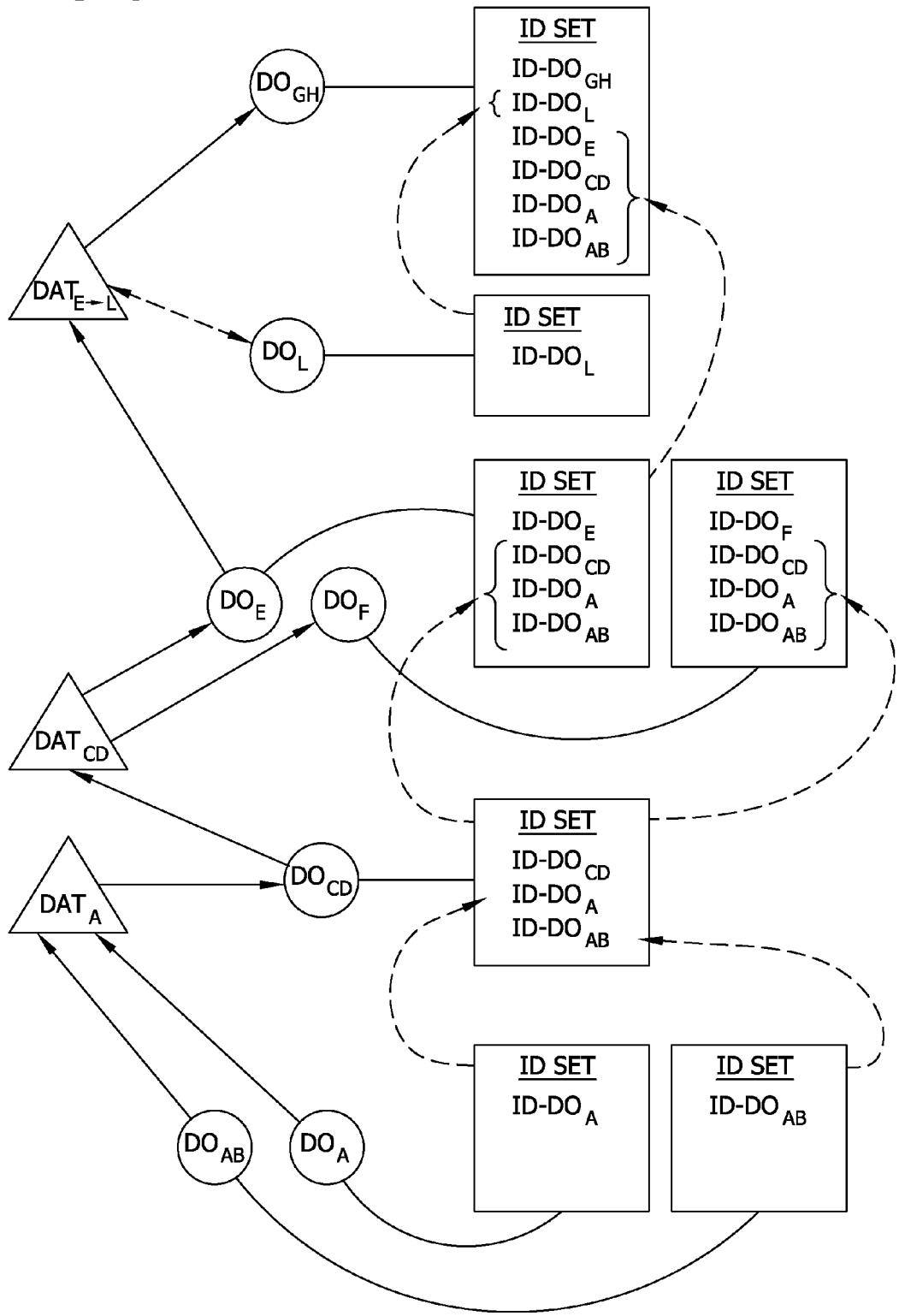
FIGS. 6A and 6B are block diagrams, each illustrating an aspect of an exemplary system model in an accordance with an embodiment of the invention.

In one embodiment, in addition to its own ID and the ID of the auxiliary DO(s) accessed by the generating DAT for the particular data object, the identifier set of each particular data object includes the ID of ancestral data object(s). Although the ID of ancestral DO(s) is discussed herein as being in addition to the ID of the auxiliary DO(s), it should be noted that the inclusion of these types of IDs in the identifier set are two distinct features and thus may be used independently/alternatively from one another. Referring to FIG. 6A, in one embodiment, the identifier set of each particular data object comprises the ID of the particular DO; and if a DAT generated the particular data object, the identifier set of the particular data object also includes the ID of any auxiliary DO accessed by the generating DAT, and the identifier set of the input data object(s) of the generating DAT. Thus, the identifier set of each particular data object generated by a DAT, includes its own ID and the IDs of each input DO and each auxiliary DO used by each DAT in the workflow to create the particular data object.

As illustrated in FIG. 6A, data objects $DO_A$ and $DO_{AB}$ are not generated by a DAT, so the identifier set for each of these data objects is comprised of its own ID. Thus, the identifier set of $DO_A$ includes ID-$DO_A$, and the identifier set of $DO_{AB}$ includes ID-$DO_{AB}$. $DO_{CD}$ is generated by $DAT_A$. $DO_A$ and $DO_{AB}$ are input data objects for $DAT_A$, and $DAT_A$ does not reference any auxiliary data objects. As such, the identifier set of $DO_{CD}$ includes its own ID (ID-$DO_{CD}$), and the identifier sets (i.e., IDs included in the identifier sets) of $DO_A$ and $DO_{AB}$ since they are the input data objects of the generating DAT. $DO_E$ and $DO_F$ are generated by $DAT_{CD}$. $DO_{CD}$ is the input data object for $DAT_{CD}$, and $DAT_{CD}$ does not reference any auxiliary data objects. Thus, the identifier sets for $DO_E$ and $DO_F$, each include the ID of the respective data object and the identifier set of $DO_{CD}$. For example, the identifier set associated with $DO_E$ accordingly includes its own unique ID (ID-$DO_E$) and the IDs of $DO_{CD}$, $DO_A$, and $DO_{AB}$ (ID-$DO_{CD}$, ID-$DO_A$, ID-$DO_{AB}$, respectively) because they were the input objects for $DAT_{CD}$ and $DAT_A$ which form the workflow that created $DO_E$. $DO_{GH}$ is generated by $DAT_{E \to L}$, to which $DO_E$ is an input data object, and $DO_L$ is an auxiliary data object. As such, the identifier set associated with $DO_{GH}$ includes its own unique ID (ID-$DO_{GH}$), the ID of $DO_L$ (ID-$DO_L$) because $DO_L$ is the auxiliary DO referenced by the generating DAT, and the identifier set of $DO_E$ (ID-$DO_E$, ID-$DO_{CD}$, ID-$DO_A$, ID-$DO_{AB}$) since $DO_E$ is the input DO of the generating DAT.

Figure 6B:
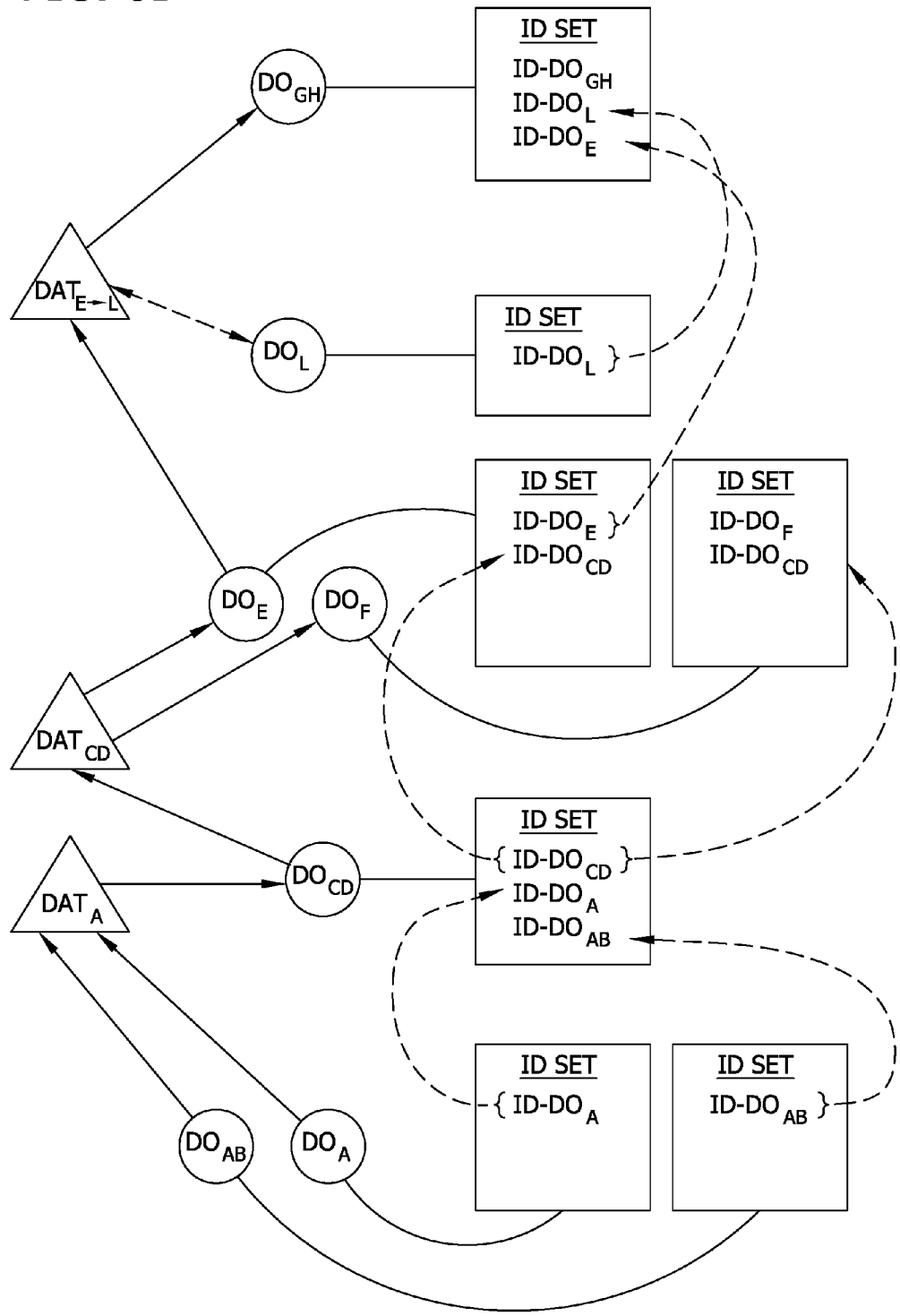

Referring to FIG. 6B, in an alternative embodiment, rather than including the entire identifier set of the input data object(s) of the generating DAT in the identifier set of the generated data object, the ancestral data for the generated data object is tracked by including just the ID of the input data object(s) of the generating DAT in the identifier set of the generated data object. Accordingly, in the illustrated embodiment, the identifier set of each particular data object comprises the ID of the particular DO; and if a DAT generated the particular data object, the identifier set of the particular data object also includes the ID of any auxiliary DO accessed by the generating DAT, and the ID of the input data object(s) of the generating DAT.

By directly associating a generated data object with the IDs of the input data objects of the generating DAT (e.g., parent data objects), the generated data object can be linked (e.g., via an ID search) to each other ancestral data object (e.g., grandparent data objects, great grandparent data objects, etc.,) in the workflow that ultimately resulted in the generation of the data object. Since the ID of the generated data object is, in turn, associated with a new data object when a new data object is created from the generated data object (e.g., the generated object functions as an input data object), the generated data object can also be linked to any children data objects.

As illustrated in FIG. 6B, data objects $DO_A$ and $DO_{AB}$ are not generated by a DAT, so the identifier set for each of these data objects includes its own ID. Thus, the identifier set of $DO_A$ includes ID-$DO_A$, and the identifier set of $DO_{AB}$ includes ID-$DO_{AB}$. $DO_{CD}$ is generated by $DAT_A$. $DO_A$ and $DO_{AB}$ are input data objects for $DAT_A$, and $DAT_A$ does not reference any auxiliary data objects. As such, the identifier set of $DO_{CD}$ includes its own ID (ID-$DO_{CD}$), and the IDs of $DO_A$ and $DO_{AB}$ (ID-$DO_A$ and ID-$DO_{AB}$) since they are the input data objects of the generating DAT. $DO_E$ and $DO_F$ are generated by $DAT_{CD}$. $DO_{CD}$ is the input data object for $DAT_{CD}$, and $DAT_{CD}$ does not reference any auxiliary data objects. Thus, the identifier sets for $DO_E$ and $DO_F$, each include the ID of the respective data object, and the ID of $DO_{CD}$ (ID-$DO_{CD}$). $DO_{GH}$ is generated by $DAT_{E \to L}$, to which $DO_E$ is an input data object, and $DO_L$ is an auxiliary data object. As such, the identifier set associated with $DO_{GH}$ includes its own unique ID (ID-$DO_{GH}$), the ID of $DO_L$ (ID-$DO_L$) because $DO_L$ is the auxiliary DO referenced by the generating DAT, and the ID of $DO_E$ (ID-$DO_E$) since $DO_E$ is the input DO of the generating DAT.

Referring generally to FIGS. 6A and 6B, tracking the data objects that are accessed in the process(es) performed to generate a particular data object provides a complete record of how the data object came into existence. This information is useful to the maintenance of the IDIS, and also enables any data object to be re-created. In one embodiment, when the ID of an auxiliary data object is added to an identifier set of a particular data object, a role name is also included in the identifier set and associated with the auxiliary data object. The role name provides a description of the reference to the auxiliary data object by the generating DAT of the particular data object. Thus, the role name distinguishes data objects that functioned as auxiliary data objects from those that functioned as input data objects with respect to the particular data object as well as distinguishes between different auxiliary DOs that may be used in the generation of the particular data object. For example, when two or more auxiliary DO(s) and/or input DO(s) used by a particular DAT have the same programming language type, a role name is necessary for these DOs in order to distinguish how the DAT used them in order to create the DO generated by the particular DAT. Accordingly, in one embodiment, each argument has a unique role name so that input DO(s) and auxiliary DO(s) for a particular DAT are unambiguously assigned to variables in the computation(s) (i.e., analysis) performed by the particular DAT. As detailed below, the data lineage information (e.g., identification of ancestral input and auxiliary DOs) provided by an identifier set of a particular data object also enables the aggregate work product produced from the particular data object to be efficiently identified.

For example, referring again to FIG. 5, all of the DOs are full text searchable. In one embodiment, the IDIS also includes a searcher 220 that searches (i.e., queries) the DO database 202 as a function of search criteria generated in response to user-input search data. The user communicates with the DO database 202, and vice versa, via a user interface 220 (e.g., a graphical user interface). For example, the searcher 220 queries the DO database 202 for all DOs having text that match search criteria (referred to as primary DOs). The unique ID (referred to as primary ID) of each of the primary DOs is identified.

According to the embodiment illustrated in FIG. 6A, the IDIS then searches the DOs in the database for DOs having identifier sets that include the primary ID. The set of search results includes each primary DO and each data object identified as having an identifier set with the primary ID. In accordance with the above discussion in connection with FIG. 6A, the identifier set of each child of the primary data object will include the primary ID. Thus, the set of search results includes the primary DO and each data object that is a child of the primary DO. So, if $DO_E$ matches the search criteria, the set of search results include $DO_E$ and $DO_{GH}$ since these are the DOs that include ID-$DO_E$. Alternatively stated, $DO_E$ is the primary DO and $DO_{GH}$ is a child DO of $DO_E$.

According to the embodiment illustrated in FIG. 6B, once a primary DO is identified as matching the search criteria, the ID of the primary DO is identified (referred to as primary ID). The IDIS then searches the DO database 202 for all DOs (referred to as attenuated DOs) that include the primary ID, and identifies the IDs (referred to as attenuated IDs) included in those attenuated DOs. Thus, if the $DO_E$ matches the search criteria, it is a primary DO, and ID-$DO_E$ is the primary ID. Data object $DO_{GH}$ is an attenuated DO because it includes the primary ID, ID-$DO_E$. The ID of the attenuated DO(s), in this case ID-$DO_{GH}$, is then identified. The IDIS iteratively searches for DOs having identified attenuated IDs until the attenuated DO(s) are DOs whose own ID is not included in any other DO that has not already been identified (i.e., the youngest child(ren) DOs are identified). According to the example, $DO_{GH}$ is the youngest child since there are no other illustrated DOs including the IDs of this DO. The primary DOs and the attenuated DOs form the set of search results. Thus, although different data lineage tracking schemes were used in FIGS. 6A and 6B, the set of exemplary search results is the same. Accordingly, the self-assembling DATs of the IDIS and the data lineage tracking enable a search for one DO relating to a search to find each DO in the workflow. As such, an aggregate work product, the possibility of existence of which is completely unknown to a user, may be provided from a search related to an initial or intermediate data object.

Figure 7:
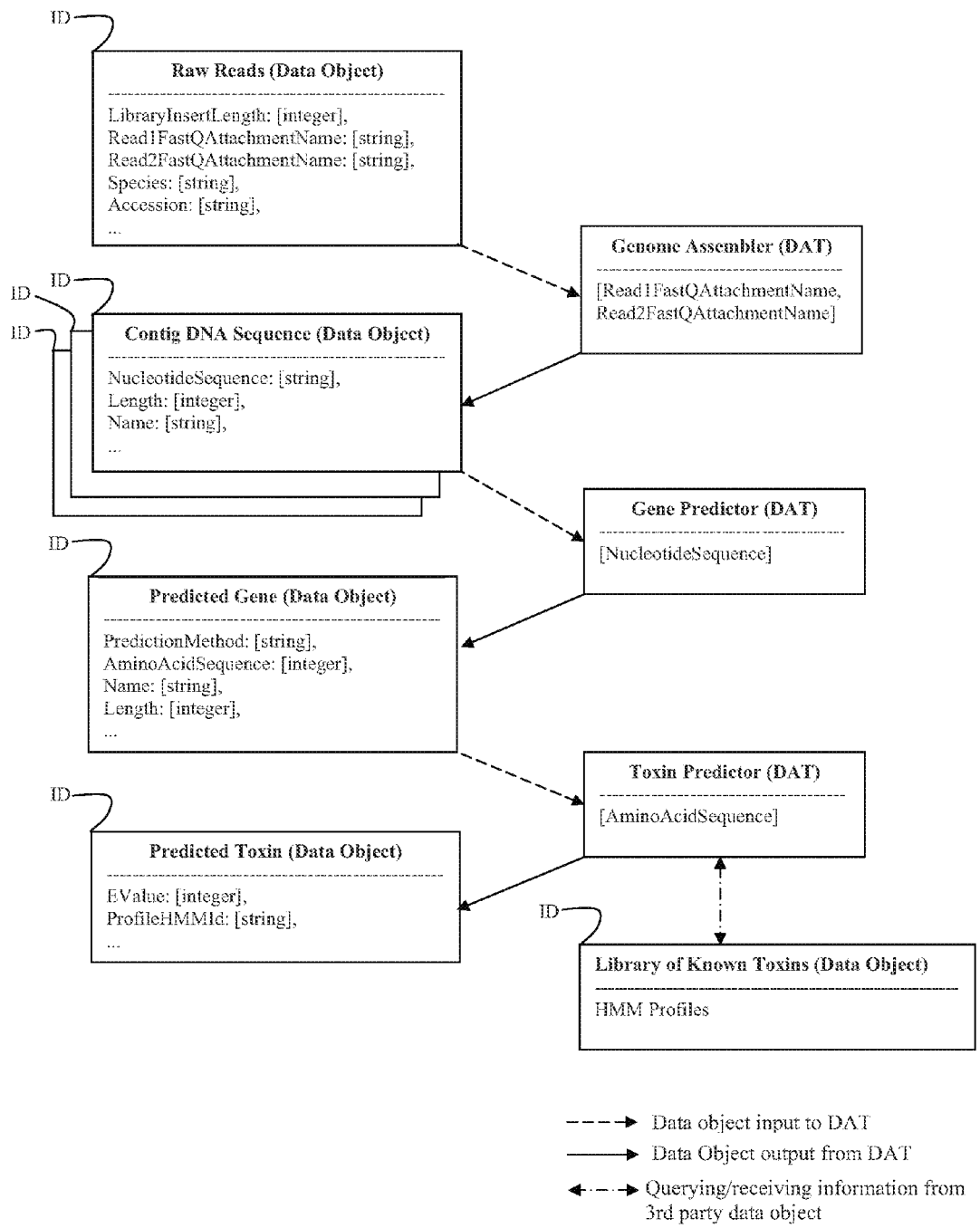
FIG. 7 illustrates a workflow for predicting toxins generated in accordance with an embodiment of the invention.

FIG. 7 illustrates a workflow for predicting toxins that is generated in accordance with an embodiment of the invention. The workflow is comprised of a plurality of independent processes. Each process comprises identifying from a potentially large data store, such as a database, a particular data object as an input data object for a particular DAT, and executing the DAT to generate a separate data object as an output data object. The processes, and thereby the DATs, link themselves together when the output data object generated in one process is used as an input data object for another process. Thus, a series of processes $P(x)$, where $x=1, 2 \ldots n$, and n is the total number of processes in the series, self assemble when a first process $P(1)$ identifies the input data object for the DAT of that process, and each subsequent process $P(x)$ (for $x>1$) identifies as an input data object, the data object that was generated as an output object from process $P(x-1)$. This is an example of a simple linear workflow, but the system is not restricted to this case. In general the system can self assemble an arbitrarily complicated web of processes, including branching, fan-in and fan-out, and cycles.

In accordance with the illustrated workflow, three independent DATs (i.e., Genome Assembler, Gene Predictor, and Toxin Predictor) are stored in a data store where they are accessible for executing as independent processes (i.e., Genome Assembler process, Genome Predictor process, and Toxin Predictor process). As explained in detail below, when a Raw Reads data object, which includes raw data from a DNA sequencer, is entered into the data store, the three independent processes (Genome Assembler process, Genome Predictor process, and Toxin Predictor process) self assemble so that at least one predicted toxin can be predicted from the Raw Reads data object.

As described above in the present disclosure, in one example a DAT listener is assigned to each DAT by the processor. Each DAT listener automatically filters the data objects in the data store based on the data attributes matching the one or more reference data attributes associated with the corresponding DAT and that have not yet been acted on or analyzed by the corresponding DAT. These filtered data objects are collected and enqueued, awaiting their turn to be processed by instances of the DAT. A multi-threaded or compute cluster implementation can run many instances each of many different DATs simultaneously. It is envisioned that in at least one embodiment of the current invention that the data analysis system will include numerous DATs vying for processing time on a computer cluster. For purposes of this example, any suitable scheduling method for allocating processing time to the respective DATs, relative to the other DATs, may be implemented. Moreover, it is also envisioned that the numerous data objects are also vying to be acted on or analyzed by the DATs. For purposes of this example, any suitable scheduling methods for prioritizing the processing of respective data objects (Ex: First In First Out or "FIFO"), relative to the other data objects, may be implemented.

Referring still to FIG. 7, the Raw Reads data object contains information relating to numerous raw DNA reads generated by sequencing a longer strand of DNA from a selected species (e.g., human, a type of bacteria, a type of plant, etc.) using a DNA sequencer, such as the Illumina HiSeq sequencer, that performs shotgun sequencing. The raw DNA reads (i.e., raw reads) are short fragments of the longer strand of DNA that are sequenced by the sequencer. As with the other data objects utilized by the data analysis system, the Raw Reads data object from the selected species is stored in the data store, such as a CouchDB database (or other similar data management system), as set forth in the above disclosure. In a document-oriented database such as CouchDB or MongoDB, the Raw Reads data object (and all other data objects in the data store) may be stored as documents, such as JSON documents. In a relational database, these may be stored as rows in a table. Each document includes a unique identification string (i.e., a stored ID including a sequence of characters), which may be assigned by the data store (or a user or a DAT) when the data object is uploaded and/or saved to the data store, a data attribute set, and some value (e.g., a particular integer, a particular string, a particular array, etc.) associated with each data attribute. As set forth in the above disclosure, the data attributes for any data object may be constrained by a predefined ontology.

In the illustrated flow diagram, the data attribute set of the Raw Data Reads the data object, as well as each other data object, is listed in the corresponding box, below the data object name. In the illustrated example, the Raw Reads data object includes the following data attributes: LibraryInsertLength, Read1FastQAttachmentName, Read2FastQAttachmentName, Species, and Accession. The Raw Reads data object may include additional data attributes. The value associated with the data attribute LibraryInsertLength relates to the length of the sheared collection of the raw DNA strands, from which the smaller reads are produced. The values associated with the Read1FastQAttachmentName and the Read2FastQAttachmentName attributes relate to all of the DNA sequences of the raw reads generated by the DNA sequencer. The attributes Species and Accession have values for identifying the species and subspecies of the DNA that was sequenced. Because the Raw Reads data object is uploaded data from an external source (i.e., data that is uploaded to the data store from outside the data analysis system and is not generated from a DAT within the system), the selected data attributes may be manually associated with the Raw Reads data object when the Raw Reads data object is uploaded into the data store. For example, a user (e.g., the person uploading the data object) may chose the data attributes from a plurality of data attributes stored in the ontology store, as described above in the present disclosure.

In the illustrated example, the DAT entitled "Genome Assembler (DAT)" is executed by the processor. The Genome Assembler DAT subscribes to the Raw Reads data object and analyzes the Raw Reads data object to generate a plurality of data objects each entitled Contig DNA Sequence (Data Object). The Genome Assembler DAT (as with all DATs in this example) is associated with a reference data attribute set, which includes one or more reference data attributes. These reference data attributes are selected from the plurality of data attributes stored in the ontology store (the same data store from which the data attributes of the data objects are chosen), and are associated with a corresponding DAT when the DAT is created. That is, the creator of the DAT selects reference data attributes from the plurality of data attributes of the ontology to form a reference data attribute set. The reference data attributes of the reference data attribute set will determine the data objects to which the corresponding DAT subscribes. In the present example, the reference data attribute set associated with the Genome Assembler DAT includes the reference data attributes Read1FastQAttachmentName and Read2FastQAttachmentName. The Genome Assembler DAT performs an operation on (e.g., analyzes) the Raw Reads data object because the Raw Reads data object includes data attributes that match each of the reference data attributes associated with each of the Genome Assembler DAT. (though the data object may additionally have data attributes and values beyond those required by the subscription).

In this example, the Genome Assembler DAT subscribes to a data object (any data object in the data store) if and only if the data attribute set of the data object includes data attributes that match each and every reference data attribute associated with the Genome Assembler DAT. The same holds true for each DAT in this example. As can be seen from this present example, the Raw Reads data object includes data attributes that do not match the reference data attributes associated with the Genome Assembler DAT, but the Genome Assembler DAT subscribes to the Raw Reads data object because each and every reference data attribute in the respective reference data attribute set is matched to a corresponding data attribute of the data object. In effect, the reference data attribute sets in this example are somewhat analogous to a Boolean search combination using the AND operator where objects are matching if they have at least that Boolean expression. That is, a match is identified if the data attribute(s) of the data object matches all reference data attributes of the DAT, regardless of whether the data object includes additional, non-matching data attributes. It is understood, as set forth above in the present disclosure, that the reference data attribute set may include reference data attributes connected (either explicitly or functional) by Boolean operators, such as OR, XOR, NAND and NOT. Moreover, as also set forth above, a "match" may be determined by identifying some semantic lexical relationship between the data attribute and the reference data attribute, such that the data attribute and the reference data attribute match even though they are not identical (e.g., the data attribute and reference data attribute may have a cognitive synonym relationship, a hyponym/hypernym relationship, or meronym/holonym relationship).

As set forth above, the Genome Assembly DAT generates a plurality of Contig DNA Sequence data objects. The Genome Assembly DAT includes a set of instructions or algorithms for analyzing the Raw Reads data object to generate the Contig DNA Sequence data objects. In general, the Genome Assembly DAT analyzes the values associated with the Read1FastQAttachmentName and Read2 FastQAttachmentName data attributes from the Raw Reads data object to determine overlapping DNA segments (referred to as "contigs") that constitute consensus regions of the DNA that was sequenced. Determining contigs is a known process involving the re-assembly of the small DNA fragments (i.e., DNA reads) that were sequenced using shotgun sequencing, for example. In one embodiment, the Genome Assembly DAT may utilize an external software program (e.g., a UNIX or web-based program) that generates the contig data. The Genome Assembly DAT uses the outputted contig data from the external software program to generate the Contig DNA Sequence data object. Each Contig DNA Sequence data object includes the data attributes NucleotideSequence, Length, and Name, among others, each of which has a value (e.g., a particular integer or a particular string) associated with it. The NucleotideSequence data attribute has a value relating to the DNA sequence of the generated contig. The Length attribute has a value relating to the length of the contig sequence, and the Name attribute has a value relating to a name of the contig sequence. As with all DATs, the Genome Assembler DAT determines the attributes that are included in the Contig DNA Sequence data objects.

Figure 8:
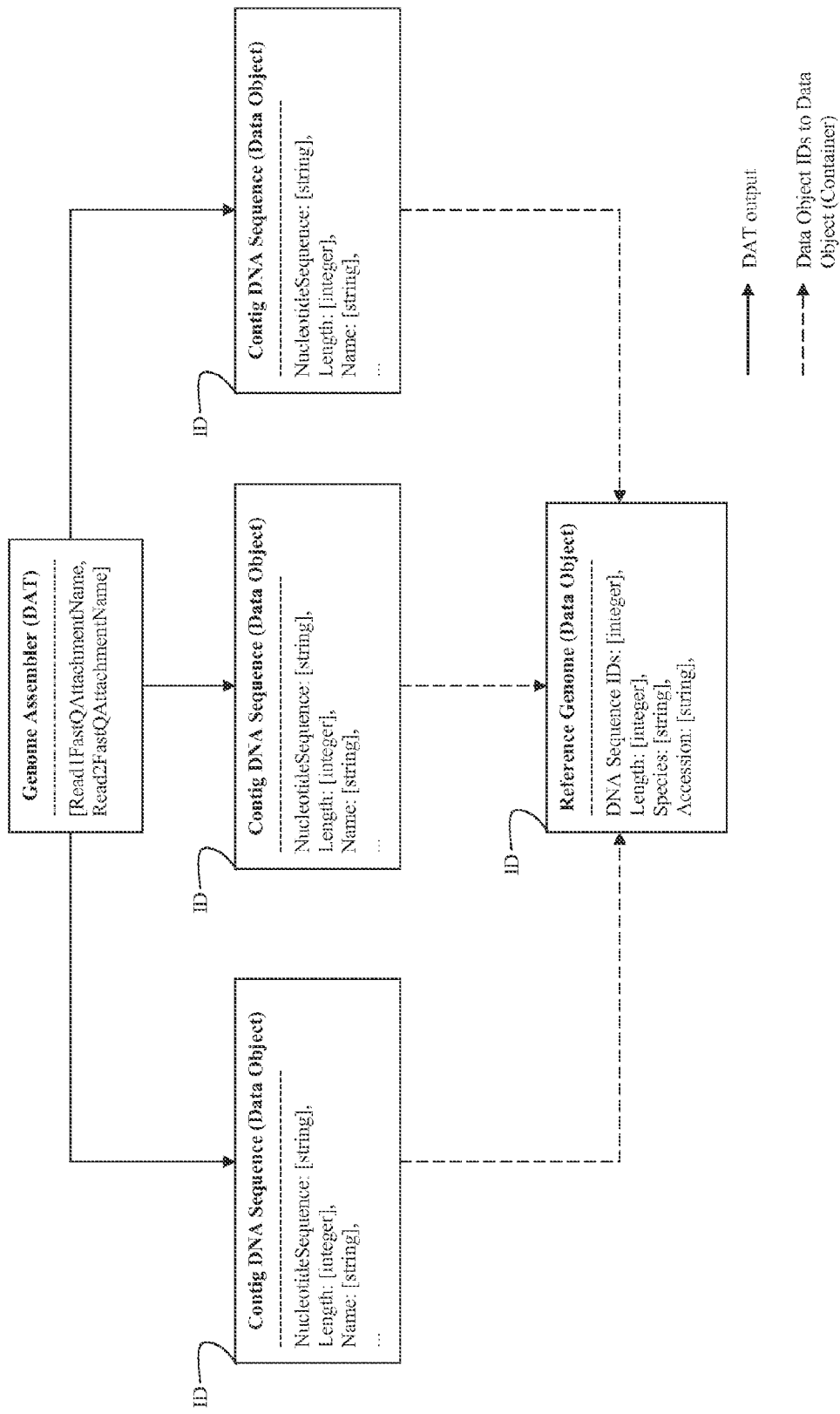
FIG. 8 illustrates one example the Gene Assembler DAT also generates a Reference Genome data object in accordance with an embodiment of the invention.

Referring to FIG. 8, in one example the Gene Assembler DAT also generates a Reference Genome data object. The Reference Genome data object functions as a container data object that stores all of the IDs of the Contig DNA Sequence data objects generated by the Gene Assembler DAT from the Raw Reads data object. The stored IDs of all of the Contig DNA Sequence in the Reference Genome data object function as pointers, which point to the Contig DNA Sequence data objects that were generated from a corresponding Raw Reads data object. In this way, the entire DNA sequence or genome that was sequenced is accessible from a single data object (e.g., JSON document).

Referring back to FIG. 6, the DAT entitled "Gene Predictor (DAT)" acts on or analyzes the Contig DNA Sequence data objects to generate data objects entitled "Predicted Gene (Data Object)." The Gene Predictor DAT subscribes to Contig DNA Sequence data objects because the data attribute NucleotideSequence, in each of the data attribute sets of the Contig DNA Sequence data objects, matches the reference data attribute NucleotideSequence associated with the Gene Predictor DAT. In the illustrated flow diagram, the Gene Predictor DAT is shown acting on or analyzing only one Contig DNA Sequence data object to generate a single Predicted Gene data object. It is understood that the Gene Predictor DAT may analyze the other Contig DNA Sequence data objects (and possibly other types of "matching" data objects) during other runs of the DAT.

The Gene Predictor DAT includes a stored set of programmed instructions or algorithms for analyzing the selected Contig DNA Sequence data object to generate the Predicted Gene data object. In general, the Gene Predictor DAT analyzes the value associated with the NucleotideSequence attribute (which contains information relating to the contig sequence) in the selected DNA Sequence data object to predict one or more genes that is encoded in the contig DNA sequence, if any such genes are present in that contig DNA sequence. The Gene Predictor DAT may include any one of a number of algorithms by which a gene contained within the selected contig DNA sequence is predicted. Known, non-limiting examples of such gene prediction algorithms include Prodigal, Augustus, FGenes. Moreover, as with the Gene Assembly DAT, the Gene Predictor DAT may utilize an external software program (e.g., UNIX or a web-based program) that generates the predicted gene data.

The Predicted Gene data object includes information relating to a gene that is predicted to be encoded in the selected contig DNA sequence contained in the Contig DNA Sequence data object. The Predicted Gene data object includes the data attributes PredictionMethod, AminoAcidSequence, Name, and Length. The value (e.g., a particular string) associated with the PredictionMethod attribute provides information regarding the prediction method that was used to generate the Predicted Gene data object. The value (e.g., a particular string) associated with the AminoAcidSequence attribute provides information relating to the amino acid sequence encoded by the predicted gene (i.e., the amino acid sequence of the protein that is translated from the predicted gene). The value of the Name attribute relates to the name of the predicted gene (this name can be created or assigned from an ontology if the predicted gene is a known gene), and the value (e.g., an integer) of the Length attribute provides information relating to the length of the predicted gene.

In the illustrated example, the DAT entitled "Toxin Predictor (DAT)" acts on or analyzes the Predicted Gene data object to generate the data object entitled "Predicted Toxin (Data Object)." The Toxin Predictor DAT subscribes to the Predicted Gene data object because the data attribute AminoAcidSequence included in the Predicted Gene data object matches the reference data attribute AminoAcidSequence associated with the Toxin Predictor DAT. In the illustrated example, the Toxin Predictor DAT is a querying DAT, which is a DAT that queries one or more auxiliary data objects (e.g., 3rd party data objects) to obtain information that is used to analyze the selected data object. In the illustrated example, the Toxin Predictor DAT queries from the set of data objects entitled "Library of Known Toxins (Data Objects)." The Library of Known Toxins data object contains information relating to known toxins, which, in the illustrated example, includes hidden Markov model (HMM) profiles of known toxin families. In general, the Toxin Predictor DAT makes a homology-based analysis of the predicted gene using the value associated with the AminoAcidSequence data attribute of the selected Predicted Gene data object and the HMM profiles in the Library of Known Toxins data object. The Toxin Predictor queries the Library of Known Toxins data object to compare the amino acid sequence encoded by the predicted gene to the HMM profiles, and calculates an E-value for each returned HMM profile. The E-value is based on the probability that the amino acid sequence is a homolog of the returned HMM profile.

The Predicted Toxin data objects include information relating to a toxin (from the Library of Known Toxins) that may be a homolog of the protein (i.e., amino acid sequence) that is encoded by the predicted gene. In the illustrated embodiment, a single Predicted Toxin data object is generated from the Toxin Predictor DAT based on the selected Predicted Gene data object. However, it is understood that more than one Predicted Toxin data object may be generated from the Toxin Predictor DAT based on a single Predicted Gene data object. That is, the Toxin Predictor DAT may determine that more than one toxin from the Library of Known Toxins data object is homologous to the amino acid sequence data included in the Predicted Gene data object. The Predicted Toxin data object includes the following data attributes: EValue and ProfileHMMId. The ProfileHMMId data attribute is the ID of the profile HMM (hidden Markov model) profile that was returned based on the comparison of the predicted amino acid sequence to the HMM profiles in the Library of Known Toxins. In essence, the ProfileHMMId is a pointer that points to the location of a data object containing the returned HMM profile. The value associated with the EValue data attribute is the calculated E-value of the comparison between the predicted amino acid sequence and the returned HMM profile, which signifies the probability that the returned HMM profile is a homolog of the predicted amino acid sequence.

As with the Genome Assembly DAT, in one example the Toxin Predictor DAT generates a plurality of Predicted Toxin data objects. As such, a separate data object (e.g., JSON document) may be created to function as a folder or container data object that stores all of the IDs of the Predicted Toxin data objects generated by the Toxin Predictor DAT from the Contig DNA Sequence data object. The stored IDs of all of the Predicted Toxin data objects in the file data object function as pointers, which point to the Predicted Toxin data objects that were generated from a corresponding Contig DNA Sequence data object. In this way, all of the toxins that were predicted from the corresponding Contig DNA sequence data object are accessible from a single data object (e.g., JSON document). An identifier set, as described above in connection with FIGS. 6A and 6B, may be associated with each of the data objects illustrated in FIGS. 7 and 8. As such, data lineage information for each of the data objects is tracked and may be used to provide useful search results in response to a user-initiated search. For example, if a user searches for a particular species (e.g., corn), and Raw Reads data objects exist in the IDIS having the particular species data attribute value, the predicted toxin data objects that are ultimately generated from those Raw Reads data objects are provided in the search result set due to the data lineage tracking.

Figure 9:
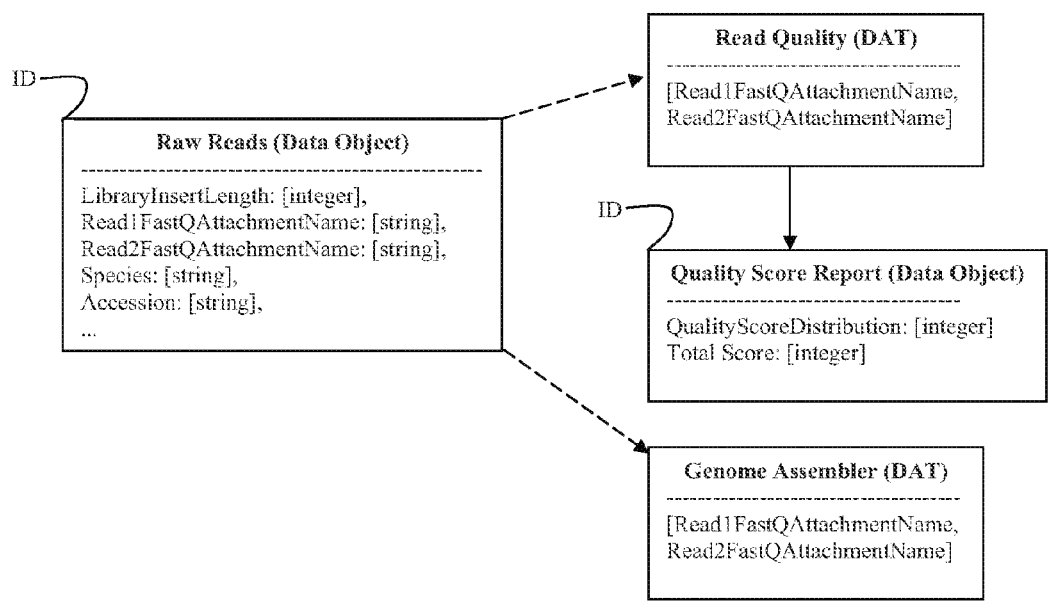
FIG. 9 illustrates an additional DAT entitled "Read Quality (DAT)" subscribes to and analyzes the Raw Reads data object (the same one from FIG. 6) to generate a data object entitled "Quality Score Report (Data Object)" in accordance with an embodiment of the invention.

Referring to FIG. 9, an additional DAT entitled "Read Quality (DAT)" subscribes to and analyzes the Raw Reads data object (the same one from FIG. 7) to generate a data object entitled "Quality Score Report (Data Object)." The Read Quality DAT subscribes to the Raw Reads data object because the data attribute set of the Raw Reads data object includes data attributes that match each and every reference data attribute (i.e., Read1FastQAttachmentName and Read2FastQAttachmentName) associated with the Quality Score Report DAT. Thus, as shown in FIG. 9, two DATs (i.e., the Read Quality DAT and the Genome Assembler DAT) subscribe to and analyze the same data object (i.e., Raw Reads data object). It is understood that other DATs may also subscribe to the Raw Reads data object.

The Read Quality DAT includes a set of programmed instructions for analyzing the Raw Reads data object to generate the Quality Score Report data object. The Read Quality DAT, as with all DATs, may be run on a processor in a computer cluster, as set forth above. In general, the Read Quality DAT analyzes the values associated with the Read1FastQAttachmentName and Read2FastQAttachmentName data attributes, according to the set of programmed instructions, to determine the quality of the raw reads generated by the DNA sequencer. In this example, the Read Quality DAT analyzes the values associated with the data attributes that match the reference data attributes associated with the Read Quality DAT, although it is understood that the DATs may analyze values associated with other data attributes other than those that match the reference data attributes associated with the corresponding DAT.

The Quality Score Report data object includes the data attributes QualityScoreDistribution and Total Score, each of which has a value (e.g., a particular integer) associated with it. The values associated with both the QualityScoreDistribution and Total Score attributes relate to the quality of the raw reads. As with all DATs, the Read Quality DAT determines the attributes that are included in the Quality Score Report. The determination of which attributes will be included in a data object that is outputted by a DAT is made when creating the DAT. In this example, no other DATs act on the Quality Score Report data object, so it may be considered an end-product data object. It is understood that the data analysis system may include other read quality DATs that subscribe to other data objects to analyze the quality of the data included in the respective data objects.

The following is one example in which the role name distinguishes data objects that functioned as auxiliary data objects from those that functioned as input data objects with respect to the particular data object as well as distinguishes between different auxiliary data objects used in the generation of a particular data object. In this example, a DAT subscribes to gene sequences (e.g., data objects generated from the Gene Predictor DAT in the prior example), with the intent of discriminating genes which interact with a particular protein receptor from those which do not interact with the particular protein receptor. Upon receiving a gene sequence as input data object, the DAT queries, as auxiliary data objects, a library (or libraries) of known gene sequences which interact with the particular protein receptor (i.e., a library known interacting gene sequences), and a library (or libraries) of known gene sequences which do not interact with the particular protein receptor (i.e., a library of known non-interacting gene sequences). The DAT aligns the input gene sequence to each of the known interacting gene sequences and each of the known non-interacting gene sequences. Based on the alignments, the DAT determines which of the known interacting gene sequence aligns most closely with the input gene sequence (e.g., a highest scoring, known interacting gene sequence) and which of the known non-interacting gene sequence aligns most closely with the input gene sequence (e.g., a highest scoring, known non-interacting gene sequence). The DAT only assigns the input gene sequence a "predicted to interact" classification if the known interacting gene sequence (i.e., the auxiliary DO) to which the input gene sequence aligns most closely is more similar to the input gene sequence (e.g., has a higher score) than the input gene sequence is to the known non-interacting gene to which the unknown protein aligns most closely.

In this example, many auxiliary DOs (i.e., all of the known interacting and non-interacting gene sequences in the respective libraries that were queried by the DAT) would be recorded. However, in addition to the input gene, the two highest scoring gene sequences (i.e., the highest scoring of the interacting gene sequences and the highest scoring of the non-interacting gene sequences) are the most important. By assigning proper role names to these highest scoring gene sequences, a scientist or a machine can determine which of these gene sequences was from the "known interacting gene sequence" library and which was from the "known non-interacting gene sequence" library. The role names are especially beneficial in this example because both of the auxiliary DOs (i.e., the known interacting gene sequence and the known non-interacting gene sequence) are of the same type (i.e., a gene sequence).

It is envisioned that IDIS, as disclosed above, may be employed in many different industries and fields, particularly those dealing with large amounts of data. IDIS can be employed to integrate, process, and analyze large amounts of data in an efficient, cost-effective manner. Below are non-limiting examples highlighting potential uses of IDIS in respective industries and fields.

Military/Intelligence: In another embodiment, there are significant defense/national security applications for IDIS including the effects of various troop deployment strategies intersected with various military response models. More saliently, data objects could be created for surveillance data collected from analysts, informants, financial transactions, satellite and drone imagery as well as other data sources to quantify and predict military and terrorist threats on a national or even local level. DATs can be developed to run object and feature detection on imagery, identify aberrant patterns in financial data and correlate these detected features with each other to identify, verify and quantify terrorist activity. Outputs could include models identified as highly predictive or specific predictions about current threats.

Insurance/Actuarial Science: In another embodiment, analytical tools for measuring health care or business practices for the area of insurance implicates, statistics, prior history as well as relevant risk management efforts in a given field of endeavor would be utilized in IDIS to improve the generation of probability analysis which informs underwriting activities. Relative to health insurance public and private data from previous health care outcomes, health care provider records in a given treatment regimen could be included along with genetic information from subscribers to assist in the generation of more useful models that can assist in underwriting activities. DATs can be developed to perform needed financial modeling, statistical analysis needed to inform actuarial decisions.

Social Media Analytics: In yet another embodiment, IDIS can be used to identify micro-demographics that respond differentially to advertisements so that advertisers could realize more value from their efforts by more precise content targeting and/or better target identification. User profiles, tweets, blogs, demographics, real estate records, and other publicly available information could be modeled as data objects along with click-through, served advertisement, and purchase histories as well as available private data. IDIS would then allow DATs to aggregate data from users who do and do not respond in various ways to different advertising efforts. DATs could extract salient words or topics from profiles, tweets, etc as well as from advertisements and the webpages of advertisers to make targeted content more acceptable and/or desirable to potential and/or targeted consumers. High performing ads or topics could be identified by DATs. To identify micro-demographics, DATs could be created to associate the topics differentially represented in data derived from users with topics differentially represented in data derived from advertisements. DATs could compile these findings into prescriptions for more precisely targeted advertising.

Operations Research/Dynamic Pricing/Revenue Management: There are a variety of uses for IDIS in dynamic pricing type systems, the most famous of which is the highly specific and continual re-pricing of airline tickets. Historical data on the number of available sets, price history for all seats, and the network of flights between cities could be modeled as data objects. DATs could compute the total profit generated for each flight, and other DATs could compute salient features of these price histories, such as whether the flight eventually sells out, the historical progress of marginal purchases by time until the flight, passenger histories, percentage of purchases with the target city as a final destination, and the percentage of tickets purchased in each fare class. Further DATs could correlate these features to more and less profitable flights. DATs could build various models of consumer behavior, and further DATs could use the more and less profitable flight features to suggest and simulate alternative pricing strategies relative to each of these consumer behavior models.

Drug Discovery/Therapeutics: Public and private data from human genome wide association studies (GWAS), mode of action studies, and other experiments can be modeled in IDIS as data objects. DATs could be developed to perform the GWAS analysis to associate traits, phenotypes, or biomarkers with genotypes. Further DATs could functionally annotate the genes in these trait-associated intervals. DATs and public data could be used to produce and rank predictions of genes in these intervals most likely to be causative for a given pathology. Public and private data on small molecule-protein binding and protein-protein binding could be used to annotate genes or reactions susceptible to intervention by small-molecule based therapies and identify potential molecules to actuate those therapies. Finally, data from clinical trials could be modeled in the system along with collected diagnostic and outcome data to be fed to DATs that can assess the success of potential drug therapies, or multi-drug regimens, predicted by previous stages of the analysis.

Medical Diagnostics/Personalized Healthcare: Patient records, patient demographics, diagnostic tests (such as blood pressure, blood glucose, genetic tests, MRI results, white cell counts, etc), administered treatments, health outcomes, insurance premiums, dietary information, patient genetics and expenditures could be modeled in IDIS as data objects. DATs could compute the expected marginal insurance payouts conditional on the each individual and baskets of diagnostic outcomes, treatment selections, and health outcomes to identify opportunities to improve care. Additional DATs could flag treatments that are significantly more effective given a set of demographics and diagnostics. DATs could identify those diagnostics not universally applied but which reveal information necessary to recommend specific treatments or individualized treatment regimens with significantly different ultimate expenditures. DATs could back-calculate the estimated loss from foregone opportunities identified by the system, and thus rank the important of implementing new guidelines or policies to alter care to minimize costs and/or enhance outcomes.

Computational Finance: IDIS could be used in computational finance for complex analysis tasks such as the design of new derivative securities with complex yet-to-be-determined risk and pricing, or the identification of arbitrage opportunities in the relative prices of historical securities. In the latter example, historical stock, option, bond, warrant, and other security prices at points in time would be modeled as data objects. DATs could compute and store price movement predictions based on previous data for individual securities or baskets of securities. Additional DATs could then relate the actual and predicted price movements of individual securities to others or to baskets of others to identify opportunities for statistical arbitrage trading strategies. DATs could also be constructed to assemble risk-efficient portfolios at points in time using a variety of strategies, and other DATs could evaluate the success of various strategies. SEC reporting or newswire data could also be modeled as data objects. Security valuation methods and implied trading strategies based on these data could be encoded as DATs and their relative performance analyzed by other DATs.

It is contemplated that there could be other configurations of the IDIS to implement the components and operations of the system model noted above. Additionally, there are various applications and industries, in addition to those discussed herein, in which the IDIS may be used.

The order of execution or performance of the operations in embodiments illustrated and described herein is not essential, unless otherwise specified. That is, the operations may be performed in any order, unless otherwise specified, and embodiments may include additional or fewer operations than those disclosed herein. For example, it is contemplated that executing or performing a particular operation before, contemporaneously with, or after another operation is within the scope of aspects.

When introducing elements of aspects or the embodiments thereof, the articles "a," "an," "the," and "said" are intended to mean that there are one or more of the elements. The terms "comprising," "including," and "having" are intended to be inclusive and mean that there may be additional elements other than the listed elements.

In view of the above, it will be seen that several advantages are achieved and other advantageous results attained.

Not all of the depicted components illustrated or described may be required. In addition, some implementations and embodiments may include additional components. Variations in the arrangement and type of the components may be made without departing from the spirit or scope of the claims as set forth herein. Additional, different or fewer components may be provided and components may be combined. Alternatively or in addition, a component may be implemented by several components.

The above description illustrates by way of example and not by way of limitation. This description enables one skilled in the art to make and use the disclosure, and describes several embodiments, adaptations, variations, alternatives and uses, including what is presently believed to be the best mode of carrying out the disclosure. Additionally, it is to be understood that the disclosure is not limited in its application to the details of construction and the arrangement of components set forth in the following description or illustrated in the drawings. The disclosure is capable of other embodiments and of being practiced or carried out in various ways. In addition, it will be understood that the phraseology and terminology used herein is for the purpose of description and should not be regarded as limiting.

Having described aspects in detail, it will be apparent that modifications and variations are possible without departing from the scope of aspects as defined in the appended claims. As various changes could be made in the above constructions, products, and methods without departing from the scope of aspects, it is intended that all matter contained in the above description and shown in the accompanying drawings shall be interpreted as illustrative and not in a limiting sense.

What is claimed is:

1. A computer-executed method for associating data objects, the method comprising:
    storing in a data store a plurality of data attributes for defining data objects;
    storing in the data store a plurality of data objects, each data object of the plurality having an attribute set comprising one or more data attributes of the plurality of stored data attributes, and each data object is associated with an identifier set comprising at least an identifier of the data object for distinguishing the data object from each other data object of the plurality of data objects;
    storing in the data store a data analysis tool (DAT), said DAT associated with at least one reference data attribute of the plurality of stored data attributes, and associated with at least one auxiliary data object of the stored plurality of data objects;
    identifying each data object of the plurality of stored data objects that has an attribute set comprising a data attribute that matches each at least one reference data attribute associated with the DAT;
    selecting at least one identified data object to be an input data object for the DAT;
    generating by the DAT a new data object as a function of the input data object for the DAT, wherein said generating comprises analyzing the input data object with reference to the at least one auxiliary data object and creating an identifier set for the new data object that includes an identifier of the new data object for distinguishing the new data object from each other data object of the plurality of data objects, and the identifier of the at least one auxiliary data object;
    storing the new data object as a data object of the plurality of data objects in the data store;
    identifying, as a primary data object, each data object in the data store that satisfies user-defined search criteria;
    identifying, as an attenuated data object, each data object in the data store that has an identifier set which includes the identifier of a primary data object; and
    rendering each primary data object and each attenuated data object as search results for the user-defined search criteria.

2. The computer-executed method of claim 1 wherein said creating an identifier set for the new data object comprises creating an identifier set for the new data object that further includes the identifier of the input data object for the DAT from which the new data object was generated.

3. The computer-executed method of claim 1 wherein said creating an identifier set for the new data object comprises creating an identifier set for the new data object that further includes each identifier included in the identifier set of the input data object for the DAT from which the new data object was created.

4. The computer-executed method of claim 1 wherein the identifier set associated with a data object is stored in said data object.

5. The computer-executed method of claim 1 wherein the identifier set associated with a data object is stored in the data store separately from said data object.

6. The computer-executed method of claim 1 wherein said generating a new data object further comprises establishing an attribute set for the new data object comprising one or more data attributes of the plurality of stored data attributes.

7. The computer-executed method of claim 6 wherein said DAT is a first DAT, and said at least one reference data attribute associated with the first DAT is an at least one first reference data attribute, and said new data object is a first new data object, and wherein the computer-executed method of claim 5 further comprises:
    storing in the data store a second DAT, said second DAT associated with at least one second reference data attribute of the plurality of stored data attributes, wherein the data attribute set of the first new data object comprises a data attribute that matches each at least one second reference data attribute;
    identifying the first new data object of the plurality of stored data objects as having a data attribute set comprising a data attribute that matches each at least one second reference data attribute;
    selecting the first new data object as an input data object for the second DAT;
    generating by the second DAT a second new data object as a function of the input data object for the second DAT, wherein said generating comprises creating an identifier set for the second new data object that includes an identifier for the second new data object for distinguishing the second new data object from each other data object of the plurality of data objects; and
    storing the second new data object as a data object of the plurality of data object in the data store.

8. The computer-executed method of claim 7 wherein said creating an identifier set for the first new data object comprises creating an identifier set for the first new data object that further includes each identifier included in the identifier set of the input data object for the first DAT from which the first new data object was created, and wherein said creating an identifier set for the second new data object comprises creating an identifier set for the second new data object that further includes each identifier included in the identifier set of the second input data object for the second DAT from which the second new data object was created.

9. The computer-executed method of claim 7 wherein said creating an identifier set for the first new data object comprises creating an identifier set for the first new data object that further includes the identifier of the input data object for the first DAT from which the first new data object was generated, and wherein said creating an identifier set for the second new data object comprises creating an identifier set for the second new data object that further includes the identifier of the input data object for the second DAT from which the second new data object was generated.

10. The computer-executed method of claim 1 wherein the identifier of the at least one auxiliary data object has a role name associated therewith, said role name providing a description of the reference to said at least one auxiliary data object by the DAT.

11. A system for associating data objects, the system comprising:
- at least one processor;
- at least one data storage device storing computer-executable instructions for execution by the processor; said data storage device:
  - storing in a data store a plurality of data attributes for defining data objects;
  - storing in the data store a plurality of data objects, each data object of the plurality having an attribute set comprising one or more data attributes of the plurality of stored data attributes, and each data object is associated with an identifier set comprising at least an identifier of the data object for distinguishing the data object from each other data object of the plurality of data objects; and
  - storing in the data store a data analysis tool (DAT), said DAT associated with at least one reference data attribute of the plurality of stored data attributes, and associated with at least one auxiliary data object of the stored plurality of data objects;

said computer-executable instructions comprising:
- instructions for identifying each data object of the plurality of stored data objects that has an attribute set comprising a data attribute that matches each at least one reference data attribute associated with the DAT;
- instructions for selecting at least one identified data object to be an input data object for the DAT;
- instructions for generating by the DAT a new data object as a function of the input data object for the DAT, wherein said generating comprises analyzing the input data object with reference to the at least one auxiliary data object and creating an identifier set for the new data object that includes an identifier of the new data object for distinguishing the new data object from each other data object of the plurality of data objects, and the identifier of the at least one auxiliary data object;
- instructions for storing the new data object as a data object of the plurality of data objects in the data store,
- instructions for identifying, as a primary data object, each data object in the data store that satisfies user-defined search criteria;
- instructions for identifying, as an attenuated data object, each data object in the data store that has an identifier set which includes the identifier of a primary data object; and
- instructions for rendering each primary data object and each attenuated data object as search results for the user-defined search criteria.

12. The system of claim 11 wherein said creating an identifier set for the new data object comprises creating an identifier set for the new data object that further includes the identifier of the input data object for the DAT from which the new data object was generated.

13. The system of claim 11 wherein said creating an identifier set for the new data object comprises creating an identifier set for the new data object that further includes each identifier included in the identifier set of the input data object for the DAT from which the new data object was created.

14. A tangible, non-transitory storage medium storing processor-executable instructions for associating data objects, said storage medium storing:
- instructions for storing in a data store a plurality of data attributes for defining data objects;
- instructions for storing in the data store a plurality of data objects, each data object of the plurality having an attribute set comprising one or more data attributes of the plurality of stored data attributes, and each data object is associated with an identifier set comprising at least an identifier of the data object for distinguishing the data object from each other data object of the plurality of data objects;
- instructions for storing in the data store a data analysis tool (DAT), said DAT associated with at least one reference data attribute of the plurality of stored data attributes, and associated with at least one auxiliary data object of the stored plurality of data objects;
- instructions for identifying each data object of the plurality of stored data objects that has an attribute set comprising a data attribute that matches each at least one reference data attribute associated with the DAT;
- instructions for selecting at least one identified data object to be an input data object for the DAT;
- instructions for generating by the DAT a new data object as a function of the input data object for the DAT, wherein said generating comprises analyzing the input data object with reference to the at least one auxiliary data object and creating an identifier set for the new data object that includes an identifier of the new data object for distinguishing the new data object from each other data object of the plurality of data objects, and the identifier of the at least one auxiliary data object;
- instructions for storing the new data object as a data object of the plurality of data objects in the data store;
- instructions for identifying, as a primary data object, each data object in the data store that satisfies user-defined search criteria;
- instructions for identifying, as an attenuated data object, each data object in the data store that has an identifier set which includes the identifier of a primary data object; and
- instructions for rendering each primary data object and each attenuated data object as search results for the user-defined search criteria.

15. The tangible, non-transitory storage medium of claim 14 wherein said creating an identifier set for the new data object comprises creating an identifier set for the new data object that further includes the identifier of the input data object for the DAT from which the new data object was generated.

16. The tangible, non-transitory storage medium of claim 14 wherein said creating an identifier set for the new data object comprises creating an identifier set for the new data object that further includes each identifier included in the identifier set of the input data object for the DAT from which the new data object was created.

17. A computer-executed method for associating data objects, the method comprising:
- storing in a data store a plurality of data attributes for defining data objects;
- storing in the data store a plurality of data objects, each data object of the plurality having an attribute set comprising one or more data attributes of the plurality of stored data attributes, and each data object is associated with an identifier set comprising at least an identifier of the data object for distinguishing the data object from each other data object of the plurality of data objects;
- storing in the data store a first data analysis tool (DAT), said DAT associated with at least one first reference data attribute of the plurality of stored data attributes, and associated with at least one auxiliary data object of the stored plurality of data objects;
- identifying each data object of the plurality of stored data objects that has an attribute set comprising a data attribute that matches each at least one first reference data attribute associated with the first DAT;

selecting at least one identified data object to be an input data object for the first DAT;

generating by the first DAT a first new data object as a function of the input data object for the first DAT, wherein said generating comprises analyzing the input data object with reference to the at least one auxiliary data object and creating an identifier set for the first new data object that includes an identifier of the first new data object for distinguishing the first new data object from each other data object of the plurality of data objects, and the identifier of the at least one auxiliary data object, wherein said generating a first new data object further comprises establishing an attribute set for the first new data object comprising one or more data attributes of the plurality of stored data attributes;

storing the first new data object as a data object of the plurality of data objects in the data store;

storing in the data store a second DAT, said second DAT associated with at least one second reference data attribute of the plurality of stored data attributes, wherein the data attribute set of the first new data object comprises a data attribute that matches each at least one second reference data attribute;

identifying the first new data object of the plurality of stored data objects as having a data attribute set comprising a data attribute that matches each at least one second reference data attribute;

selecting the first new data object as an input data object for the second DAT;

generating by the second DAT a second new data object as a function of the input data object for the second DAT, wherein said generating comprises creating an identifier set for the second new data object that includes an identifier for the second new data object for distinguishing the second new data object from each other data object of the plurality of data objects; and storing the second new data object as a data object of the plurality of data object in the data store.

\* \* \* \* \*